(12) United States Patent
Atencia-Fernandez

(10) Patent No.: US 11,473,153 B2
(45) Date of Patent: Oct. 18, 2022

(54) DEVICE AND METHODS OF USING DEVICE FOR SEPARATION OF BACTERIA FROM COMPLEX SAMPLES

(71) Applicant: UNIVERSITY OF MARYLAND, COLLEGE PARK, College Park, MD (US)

(72) Inventor: Francisco Javier Atencia-Fernandez, Bethesda, MD (US)

(73) Assignee: UNIVERSITY OF MARYLAND, COLLEGE PARK, College Park, MD (US)

( * ) Notice: Subject to any disclaimer, the term of this patent is extended or adjusted under 35 U.S.C. 154(b) by 672 days.

(21) Appl. No.: 15/315,978

(22) PCT Filed: Jun. 2, 2015

(86) PCT No.: PCT/US2015/033848
§ 371 (c)(1),
(2) Date: Dec. 2, 2016

(87) PCT Pub. No.: WO2015/187745
PCT Pub. Date: Dec. 10, 2015

(65) Prior Publication Data
US 2017/0121758 A1 May 4, 2017

Related U.S. Application Data

(60) Provisional application No. 62/051,127, filed on Sep. 16, 2014, provisional application No. 62/006,432, filed on Jun. 2, 2014.

(51) Int. Cl.
*C12Q 1/68* (2018.01)
*G01N 15/10* (2006.01)
(Continued)

(52) U.S. Cl.
CPC ........ *C12Q 1/689* (2013.01); *B01L 3/502753* (2013.01); *G01N 15/06* (2013.01);
(Continued)

(58) Field of Classification Search
CPC combination set(s) only.
See application file for complete search history.

(56) References Cited

U.S. PATENT DOCUMENTS 5,208,161 A * 5/1993 Saunders ............. B01D 61/142
210/232
5,284,753 A * 2/1994 Goodwin, Jr. ..... G01N 33/5005
435/29
(Continued)

FOREIGN PATENT DOCUMENTS

EP 2163880 3/2010

OTHER PUBLICATIONS https://www.corning.com/worldwide/en/products/life-sciences/products/permeable-supports/transwell-guidelines.html (Year: 2021).*
(Continued)

*Primary Examiner* — Brian R Gordon
(74) *Attorney, Agent, or Firm* — Ballard Spahr LLP; John A. Zurawski

(57) ABSTRACT

The present disclosure relates to devices and systems for separating motile pathogenic bacterial cells from samples. The disclosure also provides for methods of determining whether a sample is contaminated by pathogenic bacteria. The devices and systems disclosed herein are useful for screening water sources, environmental testing sites, food sources, and bodily fluids for the presence, absence, or quantity of bacterial cells in a sample representative of the screened sources.

16 Claims, 33 Drawing Sheets

(51) Int. Cl.
*B01L 3/00* (2006.01)
*C12Q 1/689* (2018.01)
*G01N 15/06* (2006.01)
*G01N 15/14* (2006.01)

(52) U.S. Cl.
CPC .. *G01N 15/1056* (2013.01); *B01L 2200/0689* (2013.01); *B01L 2200/0694* (2013.01); *B01L 2300/0681* (2013.01); *B01L 2300/0816* (2013.01); *B01L 2300/0864* (2013.01); *B01L 2300/12* (2013.01); *B01L 2300/165* (2013.01); *B01L 2400/0472* (2013.01); *G01N 2015/1006* (2013.01); *G01N 2015/1081* (2013.01); *G01N 2015/1486* (2013.01)

(56) References Cited

U.S. PATENT DOCUMENTS

| | | | | |
|---|---|---|---|---|
| 5,514,555 | A * | 5/1996 | Springer | A61P 37/00 435/7.24 |
| 2004/0229349 | A1* | 11/2004 | Daridon | C12M 23/16 435/305.2 |
| 2004/0256318 | A1* | 12/2004 | Iida | B01D 61/28 210/511 |
| 2013/0068310 | A1 | 3/2013 | Sip | |
| 2016/0067710 | A1* | 3/2016 | Larsen | B01L 3/502753 702/19 |
| 2017/0021350 | A1* | 1/2017 | Goodwin, Jr. | B01L 3/502746 |
| 2019/0184394 | A1* | 6/2019 | Sticker | C12M 23/20 |

OTHER PUBLICATIONS https://www.neuroprobe.com/product-category/chemotaxis_chambers/ (Year: 2021).*
https://www.neuroprobe.com/product/a3bp48-three-tiered-chemotaxis-chamber/ (Year: 2021).*
Boyden, Stephen, "The Chemotactic Effect of Mixtures of Antibody and Antigen on Polymorphonuclear Leucocytes", The Journal of Experimental Medicine, Mar. 1, 1962, pp. 453-466.
International Search Report of co-pending PCT International Application No. PCT/US2015/033848, dated Aug. 26, 2015, 3 Pages.
Written Opinion of co-pending PCT International Application No. PCT/US2015/033848, dated Aug. 26, 2015, 5 Pages.
Judith P. Armitage et al, "A simple, quantitative method for measuring chemotaxis and motility in bacteria", PloS one, Sep. 1, 1977, pp. e15309-202, XP055431365.
Diao Jinpian et al, "A three-channel microfluidic device for generating static linear . . . ", Lab on A, Royal Society of Chemistry, vol. 6, No. 3, Dec. 13, 2005, pp. 381-388.
Cheng Shing-Yi et al, "A hydrogel-based microfluidic device for the studies . . . ", Lab on A Chip, Royal Society of Chemistry, vol. 7, No. 6, Apr. 4, 2007, pp. 763-769.
Y. Kalinin et al, "Responses of *Escherichia coli* bacteria to two opposing chemoattractant gradients . . . ", Journal of Bacteriology, vol. 192, No. 7, Jul. 29, 2010, pp. 1796-1800.
Vinay V. Abhyankar et al, "Characterization of a membrane-based gradient generator for use in cell-signaling studies", Lab on A Chip, vol. 6, No. 3, Feb. 1, 2006, p. 389.
Ulrike Haessler et al, "An agarose-based microfluidic platform with a . . . ", Biomedical Microdevices, Kluwer Academic Publishers, vol. 11, No. 4, Apr. 3, 2009, pp. 827-835.
Hongkai Wu et al, "Generation of complex, static solution gradients in . . . ", Journal of the American Chemical Society, vol. 128, No. 13, Mar. 10, 2006, pp. 4194-4195.

* cited by examiner

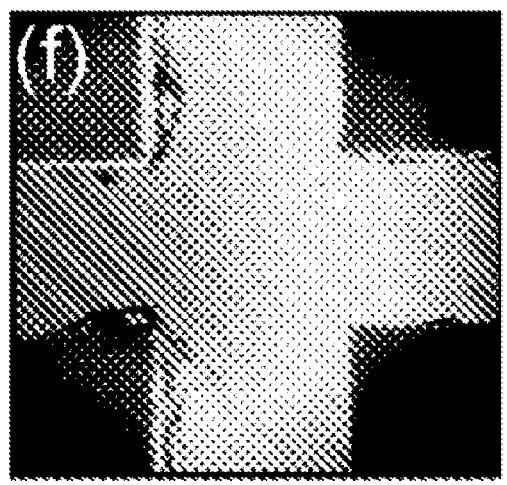 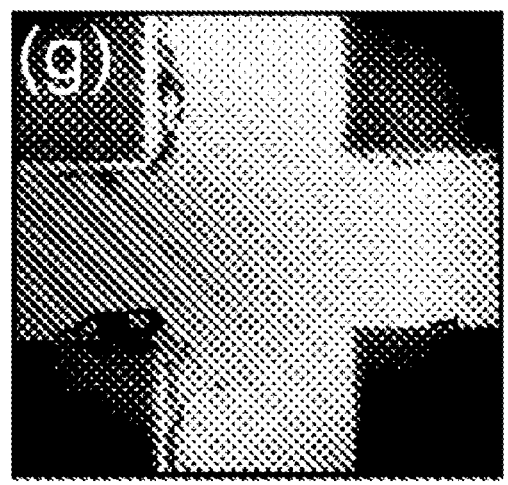
FIG. 3F  FIG. 3G
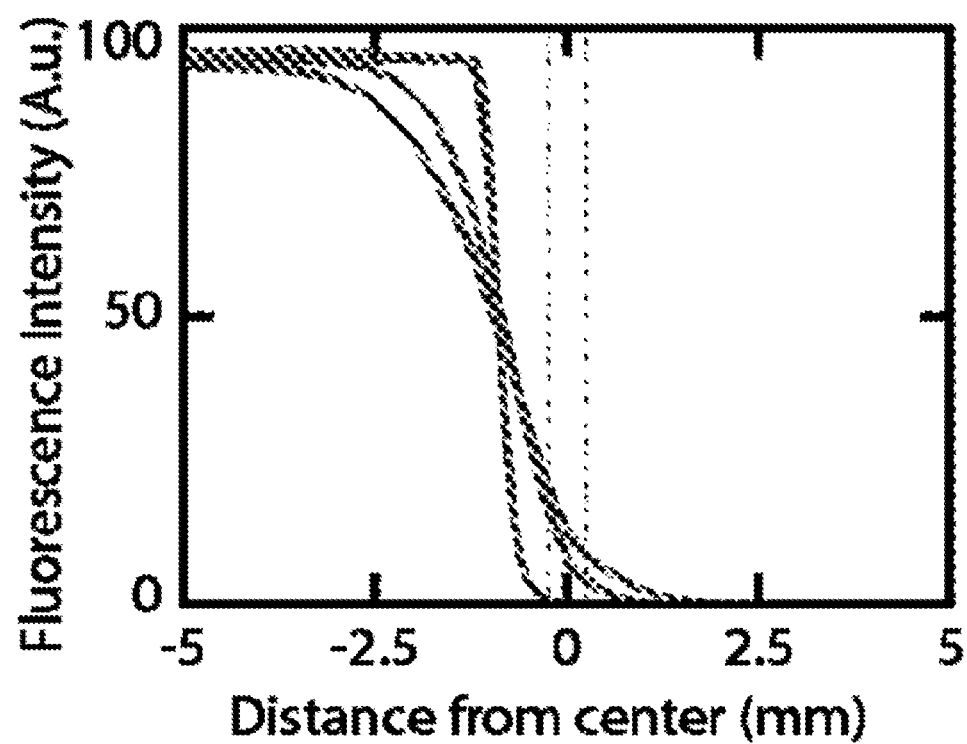
FIG. 3H

Study bacterial detachment

Study bacterial random motility

Study bacterial chemorepellence
in liquid extract from complex samples

Study selective chemotaxis

Study multi-chemotactic separations

C

E

F

G

H

DEVICE AND METHODS OF USING DEVICE FOR SEPARATION OF BACTERIA FROM COMPLEX SAMPLES

CROSS-REFERENCE TO RELATED APPLICATIONS

This application is a United States non-provisional application filed under 35 § 120, which claims priority to and is a United States National Stage filing under 35 U.S.C. § 371 of international PCT Application Serial No. PCT/US2015/033848, filed Jun. 2, 2015, which claims priority to U.S. Provisional Ser. No. 62/006,432, tiled Jun. 2, 2014, and U.S. Provisional Ser. No. 62/051,127, filed Sep. 16, 2014, each of which is incorporated herein by reference in its entirety.

GOVERNMENT SUPPORT

This invention was made with government support under 70NANB11H191 awarded by the National Institute of Standards and Technology (NIST). The government has certain rights in the invention.

FIELD OF THE INVENTION

The disclosure relates generally to devices that are capable of separating bacteria from complex samples. The present disclosure specifically relates to a device that uses chemotaxis to allow bacteria to self-separate across a membrane. The present disclosure also specifically relates to a method of identifying bacteria that have self-separated from a complex sample by chemotaxis.

BACKGROUND

Separation of bacteria from complex samples constitutes a difficult engineering problem with important ramifications to food safety and health care. Not only pathogenic and non-pathogenic bacteria are morphological very similar and small (around 2 microns in diameter), but also, very low concentration of bacteria (e.g. 10 Colony Forming Units, CFU) can pose real threats to human health. Current technologies for bacterial detection rely on DNA analysis and can be fast (e.g. polymerase chain reaction, PCR) if the bacterial count is large enough and if bacteria are suspended in "clean samples". But real samples are complex (e.g. feces, food, and blood) and the often contain solid particulates, biopolymers, fibers, foreign DNA, eukaryotic cells, and a myriad of non-pathogenic bacteria that make the direct use of PCR impractical. Therefore, sample preprocessing (1-2 days) is almost always required, including mechanical separation (e.g. separation by centrifugation) and bacterial enrichment in selective media to increase bacterial count and raise the signal to noise ratio. Transformative technologies for the rapid separation of low count of bacteria from complex samples would allow to address the current bottleneck in bacterial detection, and could have a profound impact in health care, food safety, water treatment, and more. To address these and other issues, the present disclosure relates to a microfluidic platform to separate bacteria using their ability to swim towards some chemical compounds (chemotaxis), thereby obviating the need for mechanical separation (as bacteria will self-separate from the complex sample), and selective enrichment.

SUMMARY OF INVENTION

The present disclosure encompasses the recognition that bacteria can be separated from complex samples using a chemoattractants or a combination of chemoattractants and chemorepellents. The present disclosure generally relates to a device that uses chambers separated by one or a plurality of membranes, in combination with chemoattractants and/or chemorepellents, to isolate bacteria found in complex samples. In some embodiments, the device can accomplish bacterial cell separation for subsequent extraction and detection without enrichment of the bacteria. The present disclosure also generally relates to methods of using said device to isolate bacteria from complex samples, then using analysis techniques, such as PCR, enzyme-linked immunosorbent assay (ELISA), probe assays, and/or bacteriophages, to identify the type(s) of bacteria present in the original complex samples without enriching or growing bacteria before such analysis techniques.

In some embodiments, complex samples containing bacteria are placed in an initial (first) chamber isolated from a receiving (second) chamber by a membrane. A combination of chemoattractants and/or chemorepellents present in the first and/or second chamber(s) creates a chemotaxis gradient that causes bacteria present in the sample in the first chamber to cross the membrane into the receiving chamber, where they are isolated and can be analyzed.

In some embodiments, the present disclosure relates to a system for detection or isolation or a bacterial cell that is free of a device that is capable of creating an electrical field within the first, second or third chambers of a magnitude and/or frequency that is sufficient to assist bacteria movement from the first chamber to the second chamber, nor the creation of a fluid pressure gradient of a magnitude that is sufficient to enable movement of a bacterial cell from the first chamber to the second chamber. In some embodiments, the chemoattractants and/or chemorepellents are present in gels or hydrogels located in or adjacent to the chambers. In some embodiments, a chemorepellent is present in a third chamber adjacent to the first chamber, or proximate to the first chamber and at a distance sufficient to allow for diffusion of the chemorepellent from the third chamber into the first chamber without exposure or the presence of a pressure gradient or electrical field that assists movement or transfer of the chemorepellent from the third chamber to the first chamber. In some embodiments, a buffer fluid is present in any of the first, second or third chambers. In some embodiments, the device comprises a buffer fluid in the first chamber, but the device is free of buffer fluid in the second or third chambers. In some embodiments, buffer fluid is in the first or second chambers but not in the third chamber. In some embodiments, the device comprises fluid in the within the device that is capable of suspending bacteria and passing through the membrane. In some embodiments, there is no buffer fluid present except for a buffer in the receiving (or second) chamber. In some embodiments, the device is free of fluid except for buffer present in the second chamber. In some embodiments, the device is free of fluid flow.

The present disclosure relates to a device comprising: (a) a first chamber; (b) a second chamber comprising a buffer solution; and (c) a membrane positioned therebetween; wherein the first chamber, second chamber, and membrane are free of an electric field within the first or second chamber; and wherein the membrane comprises a pore size and/or is of a thickness sufficient to allow the buffer solution to diffuse across the membrane into the first chamber, thereby creating a gradient at or proximate to the membrane surface. The present disclosure relates to a device comprising: (a) a first chamber; (b) a second chamber comprising a buffer solution; and (c) a membrane positioned therebetween; wherein the first chamber, second chamber, and membrane are free of an electrode capable of creating an electric field within the first or second chamber; and wherein the membrane comprises a pore size and/or is of a thickness sufficient to allow the buffer solution to diffuse across the membrane into the first chamber, thereby creating a gradient at or proximate to the membrane surface. In some embodiments, bacteria present in the first chamber, attracted and/or repelled by the gradient, are capable of moving across the membrane into the second chamber. In some embodiments, the device is free of a pressure source that, when in operation, is capable of creating increased pressure within the first chamber sufficient to transfer a volume of fluid from the first chamber to the second chamber. In some embodiments, the device is free of any member capable of creating microfluidic flow within the first chamber.

In some embodiments, the first chamber comprises a sample. In some embodiments, the first chamber comprises a microfluidic sample. In some embodiments, the first chamber has at least one fluid opening and a movable seal. In some embodiments, the first chamber has at least a second fluid opening. In some embodiments, the first chamber has a volume from about 25 milliliters (mL) to about 100 mL. In some embodiments, the first chamber has a volume from about 50 mL to about 100 mL. In some embodiments, the first chamber has a volume from about 100 mL to about 200 mL. In some embodiments, the first chamber has a volume from about 100 mL to about 300 mL. In some embodiments, the first chamber has a volume from about 200 mL to about 400 mL. In some embodiments, the first chamber has a volume from about 225 mL to about 500 mL. In some embodiments, the first chamber has a volume from about 225 mL to about 400 mL. In some embodiments, the first chamber has a volume from about 225 mL to about 300 mL. In some embodiments, the first chamber has a volume from about 225 mL to about 275 mL. In some embodiments, the first chamber has a volume from about 225 mL to about 250 mL. In some embodiments, the first chamber has a volume of no less than 100, 150, 200, 225, or 250 mL.

In some embodiments, the second chamber has at least one fluid opening and a movable seal. In some embodiments, the second chamber contains a growth media and/or agar with a chemotactic medium. In some embodiments, the second chamber contains a growth media and/or agar without a chemotactic medium. In some embodiments, the second chamber comprises an impeller or stir bar. In some embodiments, the second chamber comprises one or a plurality of chemoattractants. In some embodiments, the second chamber comprises one or a plurality of chemoattractants with or without chemorepellents.

In some embodiments, the device comprises a first compartment and a second compartment, wherein the first compartment has a single opening or inlet with a movable seal and the second compartment comprises a volume defined at least partially by a membrane positioned between the portion of the second compartment which is closest to the first compartment In some embodiments, the device further comprises a repellant layer adjacent to or proximate to the first chamber. In some embodiments, the repellant layer comprises a fluid-filled chamber. In some embodiments, the repellant layer comprises a gel or hydrogel. In some embodiments, the repellant layer comprises a membrane adjacent to the first chamber and defines an interface between the repellant layer and the first chamber. In some embodiments, the repellant layer comprises one or more chemorepellents. In some embodiments, the repellant layer comprises from about 1 to about 13 chemorepellents chosen from: acetate, aspartate, benzoate, leucine, phenol, tryptophan, valine, H+, OH−, citrate, maltose, $Co^{2+}$, and $Ni^2$.

In some embodiments, the first chamber and the second chamber are parallel or substantially parallel relative to the earth, with the membrane positioned in between. In some embodiments, the first chamber, the second chamber, and the repellant layer are horizontally aligned in parallel or substantially parallel layers such that the first chamber is position between the repellant layer and the second chamber. In some embodiments, the first chamber is from about 1 to about 10 millimeters in height. In some embodiments, the second chamber and the repellant layer are from about 1 millimeters to about 10 millimeters in height. In some embodiments, the first chamber is no less than 25 milliliters of volume.

In some embodiments, each of the first chamber, the second chamber, and the repellant layer comprise an independently addressable fluid inlet with a removable seal for receiving fluid.

In some embodiments, the membrane positioned between the first chamber and the second chamber covers the entire interface between the first chamber and the second chamber, such that the only fluid communication between the first chamber and the second chamber is through the pores of the membrane. In some embodiments, the device comprises a sample, such as a piece of meat or food or water, with one or a plurality of pathogenic bacterial cells. In some embodiments, the device is capable of separating the pathogenic bacterial cells from the sample by chemotaxis alone and the device is free of a source of a mechanical, electrochemical, an/or electrical force sufficient to move the pathogenic bacterial cells from the first chamber to the second chamber in the presence or absence of a chemoattractant gradient disclosed herein.

The present disclosure also relates to a kit comprising a first container comprising: (i) a first frame defining a compartment configured to receive one or a plurality of samples; (ii) a second frame defining a second compartment at least partially filled with a buffer and/or chemoattractant; and (iii) a membrane positioned therebetween. In some embodiments, the present disclosure also relates to a kit comprising a first container comprising: (i) a first frame defining a compartment configured to receive one or a plurality of samples; (ii) a second frame defining a second compartment configured for receiving a buffer and/or chemoattractant; and (iii) a membrane positioned therebetween; and a second container comprising a buffer and/or chemoattractant. In some embodiments, the kit further comprises a container comprising a chemorepellent solution or gel.

In some embodiments, the membrane is from about 3 μm to about 50 μm in thickness. In some embodiments, the membrane comprises pore sizes from about 5 μm to about 100 μm wide. In some embodiments, the membrane comprises a pore density from about $4 \times 10^4$ pores/cm$^2$ to about $4 \times 10^5$ pores/cm$^2$.

In some embodiments, the first chamber has a volume from about 25 mL to about 100 mL. In some embodiments, the second chamber has a volume from about 25 mL to about 90 mL. In some embodiments, the second chamber has a volume from about 25 mL to about 80 mL. In some embodiments, the second chamber has a volume from about 25 mL to about 70 mL. In some embodiments, the second chamber has a volume from about 25 mL to about 60 mL. In some embodiments, the second chamber has a volume from about 25 mL to about 50 mL. In some embodiments, the second chamber has a volume from about 25 mL to about 40 mL. In some embodiments, the second chamber has a volume from about 25 mL to about 30 mL. In some embodiments, the first chamber has a volume no less than 25, 30, 35, 40, 45, 50, 55, 60, 65, 70, 75, 80, 85, 90, 95, 100, 110, 120, 125, 130, 140, 150, 160, 170, 180, 190, 200, 225, 250, 275, or 300 mL.

In some embodiments, the disclosure relates to a kit comprising: (a) a first container comprising: (i) a first frame defining a first compartment configured to receive one or a plurality of samples; (ii) a second frame defining a second compartment at least partially filled with a buffer and/or chemoattractant; and (iii) a membrane positioned therebetween; and (b) a second container comprising a chemorepellent solution or gel configured for secure placement at or proximate to the first compartment such that the distance between the first compartment and the chemorepellent solution or gel is sufficient to allow diffusion of the chemorepellent from the gel or liquid into the first compartment.

The present disclosure also relates to a method of isolating a pathogen from a sample comprising: placing one or a plurality of samples into the first chamber of any of the devices disclosed herein; and allowing a time period to elapse sufficient for any pathogen in the one or plurality of samples to move from the first chamber to the second chamber. In some embodiments, the present disclosure also relates to a method of detecting a pathogen in a sample comprising: placing one or a plurality of samples into the first chamber of any of the devices disclosed herein and contacting the one or plurality of samples to the membrane; and allowing a time period to elapse sufficient for any pathogen in the one or plurality of samples to move from the first chamber into the second chamber. In some embodiments, the time period is no more than 35, 34, 33, 32, 31, 30, 29, 28, 27, 26, 25, 24, 23, 22, 21, or 20 minutes.

The present disclosure also relates to a method of manufacturing a device capable of separating motile bacterial cells comprising tightening a membrane over an opening to a chamber, aligning a second chamber over the first chamber, and introducing a solution or buffer comprising a one or a plurality of chemoattractants selective for one or a plurality of motile bacterial into the first chamber and at a concentration sufficient to draw the one or plurality of motile bacteria from the second chamber to the first chamber. In some embodiments, the method further comprises milling plastic prior to aligning the chambers or tightening the membrane over a chamber such that the plastic piece is of any of the dimension provided in his disclosure.

In some embodiments, the method further comprises extracting the pathogen from the second chamber after allowing the time period to elapse. In some embodiments, the method further comprises extracting genomic nucleic acid from the pathogen after extracting the pathogen from the second chamber. In some embodiments, the method further comprises detecting the presence or absence of a pathogen by performing a polymerase chain reaction after extracting the genomic nucleic acid from the pathogen. In some embodiments, the method is performed in less than 14 hours.

In some embodiments the method further comprises the step of exposing the one or plurality of samples to a gradient of chemoattractants and/or chemorepellents; after placing the sample in the first chamber but before or contemporaneous with allowing the time period to elapse. In some embodiments, the one or plurality of samples comprises a solid or semi-solid matrix. In some embodiments, the one or plurality of samples comprises a liquid wash from crop material. In some embodiments, the one or plurality of samples comprises concentrated fluid.

BRIEF DESCRIPTION OF THE DRAWINGS

FIG. 2A depicts a schematic showing how fluid-flow gradient generators work. FIG. 2B depicts a picture of a microfluidic device. FIG. 2C depicts data collected from the microfluidic device without the use of chemorepellent. FIG. 2D depicts data collected from the microfluidic device with the use of a chemorepellent.

FIGS. 3A, 3B, 3C, 3D, 3E, 3F, 3G, 3H, 3I, and 3J depict diagrams of and data from a device that generates chemotaxis gradients in the absence of fluid-flow. FIGS. 3A, 3B, 3C, 3D, and 3E depict the addition of dye and buffer to the device. FIGS. 3F and 3G depict the evolution of the chemical gradient at the channel intersections of the device. FIG. 3H depicts a graph of the temporal evolution of the chemical gradient. FIG. 3I depicts the introduction of fluorescein to the device. FIG. 3J depicts a graph of the distribution of fluorescein over time.

FIG. 4A depicts a diagram of a chemotaxis device. FIG. 4B depicts the chemorepellance of bacteria from ethanol. FIG. 4C depicts a graph detailing the movement of the bacteria away from the ethanol gradient.

FIG. 5A depicts a device that can accommodate more than three chemical sources. FIG. 5B depicts the movement of bacteria towards a glucose chemoattractant.

FIG. 6A depicts the introduction of a bacterial sample. FIG. 6B depicts the exposure to a chemical gradient. FIG. 6C depicts the parallelization of the assay.

FIG. 7A depicts a diagram of separating pathogenic and non-pathogenic bacteria from a complex matrix using a chemical gradient. FIG. 7B depicts a diagram of the adherence and release of bacterial cells from solids in complex samples. FIG. 7C depicts a diagram of the random motility of bacteria. FIG. 7D depicts a diagram of separating pathogenic and non-pathogenic bacteria from a complex sample.

FIG. 8A depicts a diagram of separating only one type of bacteria using a chemoattractant. FIG. 8B depicts a diagram of separating two types of bacteria using two chemoattractants. FIG. 8C depicts a diagram of separating three types of bacteria using three chemoattractants.

FIG. 9A depicts a diagram and a picture of a microfluidic chip with four channels that overlap in the vertical direction. FIG. 9B depicts a graph showing the separation and isolation of *S. typhimurium* using the chemoattractant aspartate.

FIG. 10A depicts a diagram of a cross section of the device. FIG. 10B depicts a diagram of a cross section of the device where each element is separated for clarity. FIG. 10C depicts a diagram of a cross section of the device detailing that the device is circular. FIG. 10D depicts a picture of the assembled device.

DETAILED DESCRIPTION OF THE INVENTION

Figure 1:
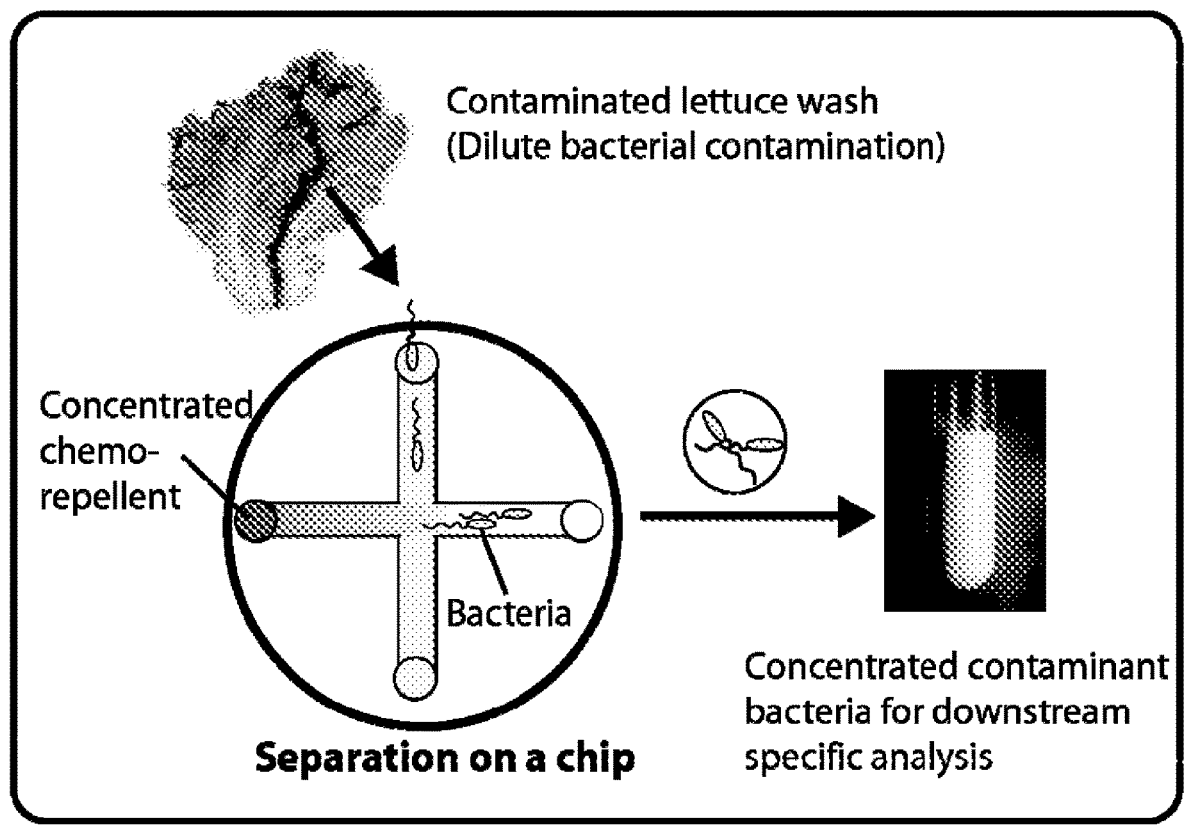
FIG. 1 depicts a concept diagram of bacterial separation using chemotaxis.

Various terms relating to the methods and other aspects of the present disclosure are used throughout the specification and claims. Such terms are to be given their ordinary meaning in the art unless otherwise indicated. Other specifically defined terms are to be construed in a manner consistent with the definition provided herein.

As used in this specification and the appended claims, the singular forms "a," "an," and "the" include plural referents unless the content clearly dictates otherwise.

The term "about" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "addressable location" as used herein means a discrete surface area or position on the biosensor from which a signal is obtained. In some embodiments, the disclosure relates to an array comprising one or a plurality of addressable locations of the biosensor with a surface no greater than 100 square millimeters. As used herein, the terms "attach," "attachment," "adhere," "adhered," "adherent," or like terms generally refer to immobilizing or fixing, for example, a group, a compound or a material, to a surface, such as by physical absorption, chemical bonding, and like processes, or combinations thereof.

As used herein the terms "electronic medium" mean any physical storage employing electronic technology for access, including a hard disk, ROM, EEPROM, RAM, flash memory, nonvolatile memory, or any substantially and functionally equivalent medium. In some embodiments, the software storage may be co-located with the processor implementing an embodiment of the disclosure, or at least a portion of the software storage may be remotely located but accessible when needed.

As used herein, "sequence identity" is determined by using the stand-alone executable BLAST engine program for blasting two sequences (bl2seq), which can be retrieved from the National Center for Biotechnology Information (NCBI) ftp site, using the default parameters (Tatusova and Madden, FEMS Microbiol Lett., 1999, 174, 247-250; which is incorporated herein by reference in its entirety).

As used herein, the terms "bodily fluid" means any fluid from isolated from a subject including, but not necessarily limited to, a blood sample, an unprocessed whole blood sample, serum sample, urine sample, mucus sample, saliva sample, and sweat sample. The sample may be obtained from a subject by any means such as intravenous puncture, biopsy, swab, capillary draw, lancet, needle aspiration, collection by simple capture of excreted fluid.

As used herein the terms "electronic medium" mean any physical storage employing electronic technology for access, including a hard disk, ROM, EEPROM, RAM, flash memory, nonvolatile memory, or any substantially and functionally equivalent medium. In some embodiments, the software storage may be co-located with the processor implementing an embodiment of the disclosure, or at least a portion of the software storage may be remotely located but accessible when needed.

The term "subject" is used throughout the specification to describe an animal from which a sample of bodily fluid is taken. In some embodiments, the animal is a human. For diagnosis of those conditions which are specific for a specific subject, such as a human being, the term "patient" may be interchangeably used. In some instances in the description of the present disclsoure, the term "patient" will refer to human patients suffering from a particular disease or disorder. In some embodiments, the subject may be a mammal which functions as a source of the isolated sample of bodily fluid. In some embodiments, the subject may be a non-human animal from which a sample of bodily fluid is isolated or provided. The term "mammal" encompasses both humans and non-humans and includes but is not limited to humans, non-human primates, canines, felines, murines, bovines, equines, and porcines.

As used herein, the term "antibody" refers to any immunoglobulin, whether natural or wholly or partially synthetically produced. In some embodiments, an antibody is a complex comprised of 4 full-length polypeptide chains, each of which includes a variable region and a constant region, e.g., substantially of the structure of an antibody produced in nature by a B cell. In some embodiments, an antibody is a single chain. In some embodiments, an antibody is cameloid. In some embodiments, an antibody is an antibody fragment. In some embodiments, an antibody is chimeric. In some embodiments, an antibody is bi-specific. In some embodiments, an antibody is multi-specific. In some embodiments, an antibody is monoclonal. In some embodiments, an antibody is polyclonal. In some embodiments, an antibody is conjugated (i.e., antibodies conjugated or fused to other proteins, radiolabels, cytotoxins). In some embodiments, an antibody is a human antibody. In some embodiments, an antibody is a mouse antibody. In some embodiments, an antibody is a rabbit antibody. In some embodiments, an antibody is a rat antibody. In some embodiments, an antibody is a donkey antibody. In some embodiments, the biosensor or system described herein comprises an antibody or plurality of antibodies.

Characteristic: As is used herein, the term "characteristic" refers to any detectable feature of a sample that allows it to be distinguished from a comparable type or control sample. In some embodiments, a characteristic is an amount or identity of an amino acid. In some embodiments, a characteristic is an amount, presence, or absence of a bacterial cell. In some embodiments, a characteristic is an amount of a small molecule, such as a chemorepellent or a chemoattractant.

The term "chemoattractant" means a chemical substance that provokes chemotaxis, and that causes a bacterium to move in the direction in which its concentration is increasing. The term is used interchangeably with the hyphenated form, "chemo-attractant"

The term "chemoeffector" as used herein refers to chemorepellents or chemoattractants.

The term "chemorepellent" means a chemical substance that provokes chemotaxis, and that causes a bacterium to move in a direction away from an increasing concentration of the substance. The term is used interchangeably with the hyphenated form ,"chemo-repellent."

Comparable: As is used herein, the term "comparable" is used to refer to two entities that are sufficiently similar to permit comparison, but differing in at least one feature.

Polypeptide: The term "polypeptide", as used herein, generally has its art-recognized meaning of a polymer of at least three amino acids. Those of ordinary skill in the art will appreciate that the term "polypeptide" is intended to be sufficiently general as to encompass not only polypeptides having the complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying or significantly reducing activity. Thus, any polypeptide that retains activity and shares at least about 30-40% overall sequence identity, often greater than about 50%, 60%, 70%, 75%, 80%, or 85%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein.

As used herein, the term "threshold value" is the concentration or number of bacteria in a sample that indicate whether the amount of bacteria in the sample is considered abnormally high or low resulting in contamination or suspected contamination of the sample. In some embodiments, information about a threshold value or reference sample of wash from crop material is obtained prior to or simultaneously with information about an experimental sample that is wash from crop material. In some embodiments, information about a threshold value or reference sample of matrix (e.g. ground meat) is obtained prior to or simultaneously with information about an experimental sample of matrix. In some embodiments, information about a threshold value or reference sample of bodily fluid is obtained prior to or simultaneously with concentration calculation or detection about an experimental sample of bodily fluid. In some embodiments, information about a reference cell or cell type is historical. In some embodiments, information about a threshold value or reference sample of bodily fluid is stored for example in a computer-readable storage medium. In some embodiments, comparison of a particular concentration value with a threshold value or reference sample of fluid or solid such as water, bodily fluid, wash or solution exposed to and collected from harvested crop material, matrix or solid meat. In some embodiments, the methods of the disclosure relate of methods of detecting the presence, absence or quantity of bacterial cells in a sample and correlating the presence, absence or quantity of the bacterial cells with a threshold value, such that if the quantity, presence or absence exceeds a threshold value for human, safety, a given sample will be determined to be contaminated and therefore unfit for human use ingestion. In some embodiments, the threshold values in different jurisdictions may vary but many of such threshold values are published by governmental authorities and are known in the art. For instance, the Food and Drug Administration of the United States has published standard guidelines for reduction of pathogenic bacteria in human food sources at http://www.f-sis.usda.gov/wps/wcm/connect/b0790997-2e74-48bf-9799-85814bac9ceb/8_IM_PR_Sal_Campy.pdf?MOD=AJPERES, the contents of which are incorporated by reference in its entireties. In some embodiments, the threshold value for what is considered a contaminated sample is those values set forth in Table 3. The purpose of comparing the quantified number of pathogenic bacterial cells in a sample to the known threshold values is to identify whether a representative sample of a larger food or water source is contaminated an unfit for human consumption. In the case of bodily fluid, the purpose is to identify whether a subject or patient may be exposed to or have an active infection. In the case of testing a blood sample, if the operator of a device or system disclosed herein identified the presence of bacterial cells, that subject may be diagnosed as having sepsis or an infection of the blood. In this case, the threshold value may be the value of 1, or s single bacterial cell.

As used herein, the term "sample" refers to a sample obtained or derived from a source of interest, as described herein. In some embodiments, a source of interest comprises an organism, such as an animal or human, or a water source or a food source, or any location where contamination is suspected or contamination is to be tested. In some embodiments, a sample is a biological sample comprising tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises bodily fluid. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by taking a representative volume of a large sample and using the smaller sample representative to changing shape or form of sample) a primary sample.

The term "motile" as used herein when describing a bacterial cell refers to a bacterial cell that is capable of moving from one location to another by its self in the case, of some embodiments, motile bacterial cells are those bacterial species that use a flagellum, axial filament or other means to self-propel. In some cases, the bacterial cells express receptors or other specialized proteins on their cell surface that guide them to or away from a particular chemical substance. The present disclosure exploits the chemotactic behaviors of bacterial cells to lures the cells into and/or repels bacteria out of different chambers or compartments of the disclosed devices or systems, thereby allowing for easier isolation and detection. Examples of motile bacterial cells include those cellular species matched with their corresponding chemoeffectos ste forth in Table 1. Other examples of motile bacteria include Some bacteria that use flagellar movement include *vibrio, spirillum, klebsiella, pseudomonas, azospirillum* and *salmonella*. Bacteria that utilize spirochaetal movement include the *borrelia, treponema, leptospira, cristispira* and *spirochaeta*. A few examples of the gliding bacteria include *achroonema, alysiella* and *cyanobacterium Oscillatoria*. Any motile bacterial cell may be separated from a sample by operation of the devices or system disclosed herein. In some embodiments, the device and systems provided herein provide methods of separating and/or detecting motile bacterial cells from and in samples that are pathogenic to humans.

In some embodiments, the present invention provides devices for detecting one or a plurality of bacterial cells and/or devices for separating motile bacterial cells from a sample. In some embodiments, the devices comprise a first chamber comprising a housing and an inlet; a seal that occludes the inlet and that is attached to the first housing; wherein the housing comprises a set of sidewalls if the housing is not cylindrical, or one cylindrical sidewall, that define a perimeter around the side of the chamber; and wherein the inlet is configured to receive a sample in liquid or solid form and wherein one portion of the first chamber is defined by a membrane, such membrane defining the interface between the first and a second chamber. In some embodiments, the second chamber comprises a concentration of chemoattractants sufficient to create a gradient of chemoattractant into the first chamber by diffusion of the chemoattractant through the membrane, whereby pathogenic bacteria in the sample that recognize the chemoattractant move from the first chamber through the membrane and into the second chamber. In some embodiments, the device is free of any external stimulus that would create a physical force sufficient to assist the motile bacterial cells in a sample to move from the first chamber to the second chamber. In some embodiments, the disclosure relates to a bacterial separation system comprising, in the following order: a chemorepellent layer, a sample chamber; a membrane, and a receiving chamber; wherein the sample chamber is not in fluid communication with the receiving chamber except for that portion of the sample chamber and the receiving chamber that share contact with the membrane. wherein the receiving chamber comprises a solution or semi-solid substance comprising a concentration of one or more chemoattractants specific to a pathogenic bacterial cell in a sample or suspected of being in a sample and sufficient to cause movement of the bacterial cell from the first chamber to the second chamber by diffusion of a gradient of chemoattractants in the first chamber. In some embodiments of the devices, the devices further comprise a housing or support member positioned at the interface between the first and second chambers that supports the membrane located between the first and second chambers. In some embodiments, the first housing further comprises a ridge positioned at or around the perimeter of the first housing that is configured for receiving and immobilizing the membrane in place. In some embodiments, the membrane is edge of the membrane and clasped to the edge of the membrane (such as depicted in FIG. 11).

Device Components and Design

The device of the present disclosure comprises at least three, four or five layers in the following order: a sample chamber with an inlet for receiving a sample, a semiporous membrane with pores from about 5 microns wide to about 100 microns wide; a second receiving chamber comprising one or a plurality of chemoattractants specific for one or a plurality of motile pathogenic bacteria. In some embodiments, a layer of one or more chemorepellents is positioned in the device in order of: the layer of one or more chemorepellents, a sample chamber with an inlet for receiving a sample, a semiporous membrane with pores from about 5 microns wide to about 100 microns wide; a second receiving chamber comprising one or a plurality of chemoattractants specific for one or a plurality of motile pathogenic bacteria, wherein the device is free of any source of electrical force (such as an electrical field) or mechanical force (such as shear stress) in the first chamber sufficient to move the pathogenic bacteria from the first chamber to the second chamber.

Membranes can be of various sizes and dimensions. In some embodiments, the membrane comprises a pore size of from about 5 to about 100 microns in width. In some embodiments, the membrane comprises a pore size of from about 5 to about 90 microns in width. In some embodiments, the membrane comprises a pore size of from about 5 to about 80 microns in width. In some embodiments, the membrane comprises a pore size of from about 5 to about 70 microns in width. In some embodiments, the membrane comprises a pore size of from about 5 to about 60 microns in width. In some embodiments, the membrane comprises a pore size of from about 5 to about 50 microns in width. In some embodiments, the membrane comprises a pore size of from about 5 to about 40 microns in width. In some embodiments, the membrane comprises a pore size of from about 5 to about 30 microns in width. In some embodiments, the membrane comprises a pore size of from about 5 to about 20 microns in width. In some embodiments, the membrane comprises a pore size of from about 5 to about 10 microns in width. In some embodiments, the membrane comprises a pore size of from about 20 to about 100 microns in width. In some embodiments, the membrane comprises a pore size of from about 20 to about 90 microns in width. In some embodiments, the membrane comprises a pore size of from about 20 to about 80 microns in width. In some embodiments, the membrane comprises a pore size of from about 20 to about 70 microns in width. In some embodiments, the membrane comprises a pore size of from about 20 to about 60 microns in width. In some embodiments, the membrane comprises a pore size of from about 20 to about 50 microns in width. In some embodiments, the membrane comprises a pore size of from about 20 to about 40 microns in width. In some embodiments, the membrane comprises a pore size of from about 20 to about 30 microns in width. In some embodiments, the membrane comprises a pore size of from about 5 to about 100 microns in width. In some embodiments, the membrane comprises a pore size of from about 5 to about 100 microns in width. In some embodiments, the width of the pore size is about 1, 2, 3, 4, 5, 6, 7, 8, 9, or 10 microns in width. In some embodiments, the membranes comprise a combination of different pore sizes ranging from about 2 microns to about 100 microns. In some embodiments, the membranes comprise a combination of different pore sizes ranging from about 1 micron to about 10 microns.

The surface area of the membrane that defines the interface between the first and second chambers may also vary. In some embodiments, the membrane covers no less than 10, 20, 30, 40, 50, 60, 70, 80, 90, 100, 110, 120, 130, 140, 150, 160, 170, 180, 190 or 200 square millimeters. In some embodiments, the surface area of the membrane greater than. 200, 300, 400, 500, 600, 700, 800, 900, or 1000 square millimeters.

In some embodiments, membranes comprise track-etched polycarbonate, polyester or polymide. In some embodiments, membranes comprise one or a combination of aluminum oxide, silver, track-etched polycarbonate, polyester or polyimide.

Pore density of the membrane may also vary. In some embodiments, the number of pores per square centimeter in the membrane is from about $4\times10^4$ pores/cm$^2$ $4\times10^5$ pores/cm$^2$. In some embodiments, the number of pores per square centimeter in the membrane is from about $5\times10^4$ pores/cm$^2$ $4\times10^5$ pores/cm$^2$. In some embodiments, the number of pores per square centimeter in the membrane is from about $6\times10^4$ pores/cm$^2$ $4\times10^5$ pores/cm$^2$. In some embodiments, the number of pores per square centimeter in the membrane is from about $7\times10^4$ pores/cm$^2$ $4\times10^5$ pores/cm$^2$. In some embodiments, the number of pores per square centimeter in the membrane is from about $8\times10^4$ pores/cm$^2$ $4\times10^5$ pores/cm$^2$. In some embodiments, the number of pores per square centimeter in the membrane is from about $1\times10^5$ pores/cm$^2$ $4\times10^5$ pores/cm$^2$. In some embodiments, the number of pores per square centimeter in the membrane is from about $2\times10^5$ pores/cm$^2$ $4\times10^5$ pores/cm$^2$. In some embodiments, the number of pores per square centimeter in the membrane is from about $3\times10^5$ pores/cm$^2$ $4\times10^5$ pores/cm$^2$. In some embodiments, the number of pores per square centimeter in the membrane is from about $4\times10^4$ pores/cm$^2$ $3\times10^5$ pores/cm$^2$. In some embodiments, the number of pores per square centimeter in the membrane is from about $4\times10^4$ pores/cm$^2$ $3\times10^5$ pores/cm$^2$. In some embodiments, the number of pores per square centimeter in the membrane is from about $4\times10^4$ pores/cm$^2$ $1\times10^5$ pores/cm$^2$. In some embodiments, the number of pores per square centimeter in the membrane is from about $4\times10^4$ pores/cm$^2$ $8\times10^4$ pores/cm$^2$. In some embodiments, the number of pores per square centimeter in the membrane is from about $4\times10^4$ pores/cm$^2$ $6\times10^4$ pores/cm$^2$. In some embodiments, the number of pores per square centimeter in the membrane is from about $4\times10^4$ pores/cm$^2$ $5\times10^4$ pores/cm$^2$. In some embodiments, the number of pores per square centimeter in the membrane is different in one portion of the membrane as compared to another portion wherein the pore density of the membrane may be range smaller number of pores in some portions and greater number of pores in other portions of the membrane.

Access to the chamber to collect or recuperate a bacterial pathogen is typically performed through an inlet and an outlet that is positioned at one or both sides of the device. The inlet and outlet could be of any shape (cylindrical or otherwise). If cylindrical in shape, the diameter of any inlet or outlet in the second chamber in some embodiments is from about 1 millimeter (mm) to about 5 mm diameter. In some embodiments, the inlet and/or outlet of the second chamber has a diameter of about 10, 20, 30, 40, 50, 60, 70, 80, 90, or 100 mm or more. Access to sample chamber can be through an inlet and an outlet, preferably as large as possible, to accommodate the volume of matrix, water, bodily fluid, or crop wash that is collected prior to any method disclosed herein. To maximize the surface area upon which the chemotactic gradient acts on the sample, large inlets to accommodate 100, 200, 300, or 400 mL of sample are contemplated by this disclosure. In some embodiments, the device or system comprises an inlet and/or outlet of more than 3 inches wide to accommodate placement and removal of the sample in the first chamber.

The size is given by the distance between membranes, from about 1 mm to about 10 mm. In some embodiments, the chamber may also not have a typical fluid inlet or outlet. Instead it will be open on its top, the sample is scooped and flattened and a semi-solid material, such as a gel with or without membrane, comprises a chemorepellent is placed on top of the flattened sample. In some embodiments, access to the repellent chamber is only needed if the repellent chamber is filled with liquid (not semisolid material). It may have an inlet and outlet like the isolation chamber, or just be open on top. In some embodiments, a kit may provide a system with three layers, in which one, two, or all three layers require insertion and fluid fill prior to exposure of the matrix or sample to the membrane. In some embodiments, the kit, system, and/or device disclosed herein is sealed such that there is no fluid flow between chambers. If the material introduced in the isolation chamber, the sample chamber and the chemorepellent chamber is semisolid, there is no need for "chambers" and the chemorepellent layer may be applied or placed on top of the sample chamber to create a "sandwich" where, on one side, the chemoattractants specific to a particular pathogenic bacterial cell draw the bacteria to the second chamber or isolation chamber and, simultaneously or substantially simultaneously, the chemorepellent layer creates a gradient which repels the bacterial cells of interest away from the chemorepellent layer. If the device or system is oriented in a parallel layers, the chemorepellent layer can repel the bacterial cells of interest toward the chemoattractant or isolation chamber.

In some embodiments, the membrane paper is of sufficient width and length to adequately overlay or obstruct the portion of the first chamber adjacent to the second chamber. In some embodiments, the membrane paper is of sufficient width and length to adequately overlay or obstruct the portion of the first chamber adjacent to the third chamber. In some embodiments, the device, system, or kit comprises a membrane between the first and second chambers and a membrane between the first and third chambers, such that when the sample is exposed to the chemotactic gradient from the second chamber, the only contact between the sample and the portions of the second or third chambers closets or most proximate to the first chamber are both membranes. In some embodiments the thickness of membrane is from about 1 micron to about 1000 microns. In some embodiments the thickness of membrane is from about 10 microns to about 900 microns. In some embodiments the thickness of membrane is from about 10 microns to about 800 microns. In some embodiments the thickness of membrane is from about 10 microns to about 700 microns. In some embodiments the thickness of membrane is from about 10 microns to about 600 microns. In some embodiments the thickness of membrane is from about 10 microns to about 500 microns. In some embodiments the thickness of membrane is from about 10 microns to about 400 microns. In some embodiments the thickness of membrane is from about 10 microns to about 300 microns. In some embodiments the thickness of membrane is from about 10 microns to about 200 microns. In some embodiments the thickness of membrane is from about 10 microns to about 100 microns. In some embodiments, the thickness of the membrane is of sufficient thickness to allow both : (i) diffusion of a gradient from one chamber to another chamber, optionally without fluid flow between chambers; and (ii) mobility of a motile bacterial cell from one chamber to the other chamber thereby separating the bacterial cell from a sample, but preventing fluid flow between the two chambers. In some embodiments, the device comprises a semipermeable membrane that is of sufficient thickness to allow both : (i) diffusion of a gradient from one chamber to another chamber, optionally without fluid flow between chambers; and (ii) mobility of a motile bacterial cell from one chamber to the other chamber thereby separating the bacterial cell from a sample, but preventing fluid flow between the two chambers.

In some embodiments, the device comprises filter paper that captures bacterial cells after they have moved for the first chamber to the second chamber. In some embodiments, the filter paper comprises one or a combination of: nitrocellulose, glass fiber, cellulose, polyester. In some embodiments the filter paper is free of cellulose, glass fiber, nitrocellulose or polyester. In some embodiments the filter paper is free of polystyrene.

In some embodiments, the systems or devices provided herein are cylindrically shaped and oriented such that the sample chamber and the second chamber (receiving chamber or isolation chamber) are aligned in parallel layers with equal or approximately equal diameters. In some embodiments, the chambers are oriented in parallel layers that have a diameter from about 5 to about 100 mm. In some embodiments, the chambers are oriented in parallel layers that have a diameter from about 5 to about 100 mm. In some embodiments, the chambers are oriented in parallel layers that have a diameter from about 20 mm to about 100 mm. In some embodiments, the chambers are oriented in parallel layers that have a diameter from about 30 mm to about 100 mm. In some embodiments, the chambers are oriented in parallel layers that have a diameter from about 40 mm to about 100 mm. In some embodiments, the chambers are oriented in parallel layers that have a diameter from about 50 mm to about 100 mm. In some embodiments, the chambers are oriented in parallel layers that have a diameter from about 60 mm to about 100 mm. In some embodiments, the chambers are oriented in parallel layers that have a diameter from about 70 mm to about 100 mm. In some embodiments, the chambers are oriented in parallel layers that have a diameter from about 80 mm to about 100 mm. In some embodiments, the first and a second chamber are cylindrically shaped and have a diameter of concentric, adjacent sides with a membrane therebetween of no less than 30 mm in diameter. In some embodiments, the first and a second chamber are cylindrically shaped and have a diameter of concentric, adjacent sides with a membrane therebetween of no less than 40 mm in diameter. In some embodiments, the first and a second chamber are cylindrically shaped and have a diameter of concentric, adjacent sides with a membrane therebetween of no less than 47 mm in diameter. In some embodiments, the first and a second chamber are cylindrically shaped and have a diameter of concentric, adjacent sides with a membrane therebetween of no less than 50 mm in diameter. In some embodiments, the first and a second chamber are cylindrically shaped and have a diameter of concentric, adjacent sides with a membrane therebetween of no less than 60 mm in diameter. In some embodiments, the first and a second chamber are cylindrically shaped and have a diameter of concentric, adjacent sides with a membrane therebetween of no less than 70 mm in diameter. In some embodiments, the first and a second chamber are cylindrically shaped and have a diameter of concentric, adjacent sides with a membrane therebetween of no less than 80 mm in diameter. In some embodiments, the first and a second chamber are cylindrically shaped and have a diameter of concentric, adjacent sides with a membrane therebetween of no less than 90 mm in diameter. In some embodiments, the first and a second chamber are cylindrically shaped and have a diameter of concentric, adjacent sides with a membrane therebetween of no less than 95 mm in diameter. In some embodiments, the first and a second chamber are cylindrically shaped and have a diameter of concentric, adjacent sides with a membrane therebetween of no less than 100 mm in diameter.

In some embodiments, the chamber that holds the sample during the separation process (in some embodiments, the first chamber) comprises a volume of from about 50 microliters to about 400 mL. If the chamber is wider than it is tall, the eight of the chamber if oriented horizontally or substantially horizontally is at least about 0.5 mm to about 10 mm. In some embodiments, the sample chamber comprises a height of about 1, about 3, about 6, or about 10 mm. The height may be determined in some embodiments by the boundaries of the second and third chambers that "sandwich" the first chamber. In some embodiments, the range of volumes for sample chamber, from about 100 microliters to about 400 mL in total volume. In some embodiments, the sample chamber comprises a total volume from about 5.0 mL to about 375 mL. In some embodiments, the sample chamber comprises a total volume from about 10.0 mL to about 375 mL. In some embodiments, the sample chamber comprises a total volume from about 125.0 mL to about 375 mL. In some embodiments, the sample chamber comprises a total volume from about 40.0 mL to about 375 mL. In some embodiments, the sample chamber comprises a total volume from about 55.0 mL to about 375 mL. In some embodiments, the sample chamber comprises a total volume from about 100.0 mL to about 375 mL. In some embodiments, the sample chamber comprises a total volume from about 150.0 mL to about 375 mL. In some embodiments, the sample chamber comprises a total volume from about 200 mL to about 375 mL. In some embodiments, the sample chamber comprises a total volume from about 250 mL to about 375 mL. In some embodiments, the sample chamber comprises a total volume of from about 300 mL to about 375 mL. In some embodiments, the sample chamber comprises a total volume of from about 20 mL to about 50 mL. In some embodiments, the sample chamber comprises a total volume of from about 25 mL to about 50 mL. In some embodiments, he sample chamber comprises a total volume of at least 100, 200, 300, or 400 or more mL.

The second chamber or isolation chamber may also be as much as range of volumes about 1.5 to 3 times the volume of the sample chamber. In some embodiments, the isolation or receiving chamber is about 50 mL to about 250 mL in total volume. In some embodiments, the isolation or receiving chamber is about 75 mL to about 250 mL in total volume. In some embodiments, the isolation or receiving chamber is about 100 mL to about 250 mL in total volume. In some embodiments, the isolation or receiving chamber is about 150 mL to about 250 mL in total volume. In some embodiments, the isolation or receiving chamber is about 200 mL to about 250 mL in total volume. In some embodiments, the isolation or receiving chamber is about 50 mL to about 400 mL in total volume. In some embodiments, the isolation or receiving chamber is about 10 mL to about 400 mL in total volume. In some embodiments, the isolation or receiving chamber is about 150 mL to about 250 mL in total volume. In some embodiments, the isolation or receiving chamber is about 250 mL to about 350 mL in total volume. In some embodiments, the isolation or receiving chamber is about 50 mL to about 100 mL in total volume. In some embodiments, the isolation or receiving chamber is about 20 mL to about 100 mL in total volume.

Similar ranges of volumes are contemplated for any volume of a third chamber or chemorepellent chamber. In some embodiments, the chemorepellent layer has a total volume of about 10 mL to about 100 mL. The third chamber or chemorepellent chamber may also be as much as range of volumes about 1.5 to 3 times the volume of the sample chamber. In some embodiments, the chemorepellent chamber is about 50 mL to about 250 mL in total volume. In some embodiments, the chemorepellent chamber is about 75 mL to about 250 mL in total volume. In some embodiments, the chemorepellent chamber is about 100 mL to about 250 mL in total volume. In some embodiments, the chemorepellent chamber is about 150 mL to about 250 mL in total volume. In some embodiments, the chemorepellent chamber is about 200 mL to about 250 mL in total volume. In some embodiments, the chemorepellent chamber is about 50 mL to about 400 mL in total volume. In some embodiments, the chemorepellent chamber is about 10 mL to about 400 mL in total volume. In some embodiments, the chemorepellent chamber is about 150 mL to about 250 mL in total volume. In some embodiments, the chemorepellent chamber is about 250 mL to about 350 mL in total volume. In some embodiments, the chemorepellent chamber is about 50 mL to about 100 mL in total volume. In some embodiments, the chemorepellent chamber is about 20 mL to about 100 mL in total volume.

In some embodiments, the total volume of the chemorepellent and/or chemoattractant (or isolation) chamber is no less than 25, 35, 45, 55, 65, 77, 85, 95, 100, 150, 200, 250, 300, 350, or 400 mL. In some embodiments, the total volume of the chemorepellent and/or chemoattractant (or isolation) chamber is no more than 25, 35, 45, 55, 65, 77, 85, 95, 100, 150, 200, 250, 300, 350, or 400 mL.

In the case of a "sandwich" type of horizontal embodiments, the systems or devices provided herein may include at least three discrete chambers in the order from top to bottom: a chamber comprising a chemorepellent (chemorepellent chamber), a chamber comprising or capable of holding a sample (a sample chamber), and a chamber comprising a chemoattractant (chemoattractant chamber), wherein a membrane disclosed herein is positioned sample chamber and the chemoattractant chamber. Although, in some embodiments, the devices and systems herein comprise only the sample chamber and chemoattractant chamber separated by a membrane. In some embodiments, one or more of the chambers comprise at least a single inlet through which a solution, sample or other substance may be introduced into the device. In some embodiments, one or more of the layers may have an inlet and an outlet, whereby the inlet and/or outlet comprises a movable seal that allows access to the internal portion of the device through a channel or conduit proximate to he inlet or outlet, respectively. When the movable seal is shut, the device becomes a closed system. For purposes of this disclosure, the term closed system refers to a system that does not have access to the open environment after each inlet or outlet is covered by a movable seal.

In some embodiments, the repellent chamber maybe filled with: (1) a given concentration of repellent ranging from about 1 mM to about 100 mM suspended in liquid (e.g. buffer with pH within a range of about pH 3 to about pH 10); (2) same liquid within a porous material (e.g. a foam or sponge); (3) with the same liquid within a gel (e.g. agar with concentration preferably 0.3 to 2%); or (4) layers of gels or porous materials containing chemical compounds that may have membranes separating the layers.

In some embodiments, the sample chamber will be filled with the food sample hat may be premixed with a suspension in buffer of: (1) a chemo repellent or chemo attractant, (2) a a chemical compound that will react with a chemo attractant or repellent (e.g. EDTA sequestering the repellent Nickel ions), (3) a compound that promotes bacterial motility and virulence (e.g. Autoinducer I, II or III) and/or (4) a compound that will turn the sample semisolid allowing the bacteria free swimming (e.g. low concentration of agar, preferably 0.3%).

In some embodiments, the isolation chamber may be filled with: (1) a suspension of a chemo attractant suspended in liquid (e.g. buffer with pH within a range of about pH 3 to about pH 10) ; or (2) with the same liquid within a gel (e.g. agar concentration 0.3 to 2%); or (3) layers of gels containing different compounds including attractants specific for the wanted bacteria and repellents for specific unwanted bacteria.

In some embodiments, the device or system disclosed herein comprises an extraction efficiency of at least about 50%, about 60%, about 70%, about 75%, about 80%, about 85%, about 90% or more.

In some embodiments, the present invention provides a system that comprises a sample collector. The sample collector can be any material that can take a sample from a source and allow the sample to be tested. For example, the sample collector can be a swab, such as a cotton-swab. In some embodiments, the sample collector is an innoculator. In some embodiments, the device comprises the sample collector and a portion of the sample collector is in the inside of the device. In some embodiments, the sample collector is partially outside and partially inside the device. In some embodiments, the sample collector is completely outside the device.

The present disclosure also provides for kits comprising the devices described herein. The kit can include a device as described herein, a sample collector, a buffer container, an instruction manual, a positive control, a negative control, or any combination thereof. With respect to the kit, a positive control is a sample that is known to contain the bacterial cell that can be detected with the device present in the kit. In contrast the negative control, would not contain an bacterial cell that can be detected by the kit. The negative control when used in conjunction with the anti-antibody would be able to demonstrate that the device is working properly.

Buffers can also be included in the one or more of the chambers to either receive motile bacterial pathogens or . Examples of buffers include, but are not limited to, 1×PBS (10 mM Phosphate, 137 mM Sodium Chloride, 2.7 mM Potassium Chloride), a wash buffer (e.g. 10 mM Sodium Phosphate, 150 mM NaCl, 0.5% Tween-20, 0.05% Sodium Azide), a membrane buffer (e.g. 10 mM Sodium Phosphate, 0.1% Sucrose, 0.1% BSA, 0.2%, PVP-40 pH 7.21, filtered with 0.2 µm filter.), Polyclonal Conjugate Block Buffer (e.g. 50 mM Borate, 10% BSA, pH 8.93); Polyclonal Conjugate Diluent (e.g. 50 mM Borate, 1% BSA, pH 9.09), or Blocking Buffers (e.g. 10 mM Sodium Phosphate, 0.1% Sucrose, 0.025% Silwet pH 7.42; 10 mM Sodium Phosphate, 1% Sucrose, 1% Trehalose, 0.01% BSA, 0.025% Tween-20; 0.05% Sodium Azide, 0.025% Silwet pH 7.4; 10 mM Sodium Phosphate, 0.1% Sucrose, 0.1% BSA, 0.2% PVP-40 pH 7.21). The buffer can also be, but is not limited to, a blocking buffer (e.g. 10% BSA in deionized water, pH 7.4 or 1% BSA in deionized water, pH 7.4); 10 mM Borate, 3% BSA, 1% PVP40, and 0.25% Tween-100; and the like.

The membrane and the second or receiving chamber can be contacted with any of the buffers described herein either in the presence or absence of a chemoattractant and/or a chemorepellent. It is understood that the disclosure relates to exposure of chemoattractants and/or chemorepellents in any combination or position within the device. In some embodiments, the sensor, device, and or system of the disclosure comprises a first chamber positioned between a second and third chamber, wherein the third chamber comprises a chemorepellent which is at a concentration sufficient to create a concentration gradient through diffusion on one side of the first chamber and the second chamber comprises a chemoattractant at a concentration that is sufficient to cause a concentration gradient of the chemoattractant through diffusion into the other side of the first chamber. It should be understood, however, that various combinations of chemoeffectors can be placed in each chamber to allow selective separation of one or a plurality of bacterial cells of interest. For instance, if the operator wishes of separate or isolate *E. Coli* strains and avoid cross contamination of the receiving chamber with other bacterial cells, the second chamber may comprise a combination of both chemoattractants specific to *E. Coli* strain but also chemorepellents that are specific for other bacterial strains that the operator wishes not to isolate. In addition, the present disclosure contemplates that the receiving chamber comprises, in some embodiments, a combination of effectors to simultaneously separate more than one pathogenic bacterial cell of choice. For instance, if the operator wants to separate pathogenic *E. Coli* strains as well as *Salmonella* strains the receiving chamber may comprise chemoattractants for both *E. Coli* and *Salmonella*. Any combination of chemoattractants or chemorepellents are contemplated by this disclosure and the combinations may be present in the third or second chambers so long as the chemoattractants corresponding to the bacterial strains that the operator desires to isolate or separate from the sample are in the receiving chamber at a concentration sufficient to create a concentration gradient in the first chamber by simple diffusion of the chemical across the membrane.

For proper operation of the device or system, it should be noted that, in some embodiments, the system or device does not comprise any source of force to pressurized fluid or create fluid communication through the membranes. In some embodiments, the system or device is free of any source of pressurized fluid of a force sufficient to cause fluid flow between any chambers. that communication through the membranes. In some embodiments, the system or device is free of any source of mechanical force sufficient to cause fluid flow between any chambers. In some embodiments, the only fluid communication between the chamber is diffusion of small chemical compounds in one or more of the chambers through the membrane or membranes positioned in between the first, second, and/or third chambers. In some embodiments, the system and device provided in the disclosure is free of a source of an electrical force sufficient to cause fluid flow between any chambers. In some embodiments, the system and device provided in the disclosure is free of a source of an electrical force sufficient to assist the movement of bacteria from one chamber to another chamber between any chambers.

Methods

It is, for example, desirable to detect and quantify in foods and agricultural products analytes that may be indicative of the freshness or quality of the food, including beverages and water supplies. In routine quality control testing of foods, it is common practice to test for the presence of various contaminants, additives, degradation products, and chemical markers of microbial infestation, e.g., bacteria, bacterial endotoxins, mycotoxins, and the like. However, current methods by which such quality control testing is accomplished are typically either complex and skill-intensive analytical chemistry, molecular biology or biochemistry procedures or highly subjective and qualitative sensory evaluations, e.g., smell test, taste test, appearance, etc.

Likewise, the ability to detect contaminants in manufacturing processes, in safety and clean up processes, in the production, collection or isolation of medically useful materials, in public drinking water systems and reservoirs, waterways, bodies of water and tidal surf can provide a warning mechanism to prevent public health threats as well as the ability to identify the source and nature of such outbreaks. Moreover, protection against the dissemination of bioterrorism and chemical warfare agents, for example, is highly desirable to ensure public safety and protection.

The present invention provides for methods of detecting an bacterial cell comprising contacting a sample with a device as described herein, wherein the sample contacts the membrane, wherein, after the step of separation, the fluid, semi-solid, or sold material in the second chamber (or receiving chamber) may be analyzed. Analysis may be performed by any known method by one of ordinary skill in the art familiar with microbiology. For instance, samples of the indicates the presence of the bacterial cell, wherein the conjugate pad comprises a first antigen-specific capture reagent and the test membrane comprises a second bacterial cell-specific capture reagent. A positive reaction is indicated by the capture reagent present in the test membrane binding to an bacterial cell in the test sample. The capture reagent in the test membrane is applied to the test membrane so that it will indicate a positive reaction when it binds to its specific bacterial cell. The specific capture reagent can be applied in any manner such that when it is detected it can form a line, a circle, a plus sign, a broken line, an "X" or any other pattern. In some embodiments, the control line indicating that the device is working properly will cross the bacterial cell specific line and when the bacterial cell specific capture reagent binds to the bacterial cell the detectable label will form a plus sign.

The present disclosure also provides for methods of separating a bacterial cell from a sample by contacting a sample in a sample chamber with a membrane positioned between the sample chamber and the isolation chamber comprising a chemoattractant. The present disclosure also provides for methods of separating a bacterial cell from a sample by contacting a sample in a sample chamber with a membrane positioned between the sample chamber and the isolation chamber comprising a chemoattractant, wherein the method further comprises allowing the sample to incubate between 15 degrees to about 30 degree Celsius for about 20, 25, 30, or 35 minutes. The present disclosure also provides for methods of separating a bacterial cell from a sample by contacting a sample in a sample chamber with a membrane positioned between the sample chamber and the isolation chamber comprising a chemoattractant, wherein the method further comprises allowing the sample to incubate between 15 degrees to about 30 degree Celsius for about 20, 25, 30, or 35 minutes, and, prior to the contacting step, sealing all of the inlets or outlets of the device except for the inlet used to introduce the sample to the sample chamber. The present disclosure also provides for methods of separating a bacterial cell from a sample by contacting a sample in a sample chamber with a membrane positioned between the sample chamber and the isolation chamber comprising a buffer and a chemoattractant, wherein the method further comprises extracting the buffer from the device and, optionally, performing a step of analysis disclosed herein to identify and/or quantify the number of bacterial cells in the isolation chamber. The present disclosure also provides for methods of separating a bacterial cell from a sample by contacting a sample in a sample chamber with a membrane positioned between the sample chamber and the isolation chamber comprising a buffer and a chemoattractant, wherein the method further comprises extracting the buffer from the device and, optionally, performing a step of analysis disclosed herein to identify and/or quantify the number of bacterial cells in the isolation chamber; wherein, before the step of extraction, all inlets and outlets of the device are sealed such that the only inlet or outlet open for access to the outside environment is the outlet through which the extraction will take place.

In some embodiments, a sample contacts the device, which is then followed by a buffer being applied to the device after the sample has contacted the membrane. For example, a sample comprising an bacterial cell can be contacted with a buffer solution to contain and such that the sample is transferred to a semi-solid or slurry maximizing the volume of sample that contacts an addressable site on the membrane. Following the contact with the buffer or other solution (also termed a reconstitution solution), the reconstitution solution comprising the samples can be applied to the device to facilitate or initiate vertical or horizontal flow through the devices described herein.

In some embodiments, the methods comprise contacting a test sample with a sample collector and contacting the sample collector with the device. In some embodiments, the methods comprise contacting the sample collector with a solution or buffer, wherein the solution or buffer is applied to the device. In some embodiments, the samples are contacted with the reconstitution solution prior to the sample coming into contact with the membrane. In some embodiments, the sample is contacted with the reconstitution solution and the membrane simultaneously.

The bacterial cell that the method can be used to detect can be any bacterial cell. The bacterial cell can be those that are discussed herein or any other bacterial cell that can be detected using the methods and devices described herein. In some embodiments, the method comprises applying the sample to the device and allowing the sample to flow through the chamber via vertical or horizontal flow. In some embodiments, the membranes between the chambers are tightened prior to introduction to sample to the device or system such that once the sample if introduced to the sample chamber there is no fluid flow from one chamber to another chamber.

In some embodiments the detection or indication of the presence or absence of an bacterial cell occurs in less than 45, 40, 35, 30, or 25 minutes. In some embodiments, the detection or indication of the presence or absence of an bacterial cell occurs in about 30 minutes.. In some embodiments, the detection or indication of the presence or absence of an bacterial cell occurs in less than 20 minutes.

The methods of the disclosure also relate to method of detecting one or a plurality of bacterial cells by performing any of the above-mentioned separation steps and further comprising analyzing the fluid in the isolation chamber by cell counter systems after extraction, by PCR after extraction, by ELISA after extraction, or in the isolation chamber by exposing the fluid and bacteria in the isolation chamber with antibodies, dyes, fluorescent antibodies, observation by microscopy, or exposure of the fluid comprising the bacterial cells with other compounds that create a signal when exposed to light or other stimulus.

Some embodiments refer to systems and methods of separating a pathogenic bacterial cell from a sample solution using chemotaxis. In some embodiments the separation of a bacterial cell from a sample occurs in less than 45, 40, 35, 30, or 25 minutes. In some embodiments, the separation of the bacterial cell from the sample occurs in about 30 minutes. In some embodiments, the separation of the bacterial cell form the sample occurs in less than 20 minutes. In some embodiments, the detection or indication of the presence or absence of an bacterial cell occurs in about 10 minutes. Some embodiments refer to systems and methods of separating a pathogenic bacterial cell from a sample solution using chemotaxis comprising steps of pre-loading or filling one, two, three, or more chambers with a suspension of the appropriate buffer comprising any one or combination of chemoeffectors, or, if, there is a fill step for the sample chamber before placement of the sample in the sample chamber, inlets described herein may be opened and suspensions comprising the buffers with or without the disclosed chemoeffectors may be injected or pipetted or poured into the device. In some embodiments, the methods of the present disclosure comprise the step of securing and/or sealing any inlet or outlet other than the inlet or outlet being used to transfer suspension, buffer or samples of fluid in or out of the system. In some embodiments, opening a single valve or seal to an outlet prior to addition or extraction of fluid from the another outlet allows for fluid flow between the chambers. In such embodiments, prior to extracting or adding any solution, buffer, suspension or sample, the methods of the disclosure comprise sealing or closing all inlets and outlets except the inlet to outlet being used to access extract or add the said solution, buffer, suspension or sample.

In some embodiments, methods disclosed relate to manufacturing the system or device disclosed herein by any of the method steps outline in the disclosure. In some embodiments, the device is manufactured by milling plastic and assembling the device according to FIG. 11. In some embodiments, the method of manufacturing the device comprises a step of mechanically stretching the membrane before attachment of the membrane to the device housing.

In some embodiments, systems and methods further comprise a step of concentrating a bacterial cell that is known to be present in a liquid. In some embodiments, systems and methods are provided to detect an bacterial cell or analyte that is known to be present in a liquid. In some embodiments, systems and methods are provided to screen a liquid to determine whether or not there is any bacterial cell or analyte present in the liquid. In some embodiments, methods are free of a step of concentrating a population of bacteria after the step of isolation or separation is complete.

Filters may be used in the second chamber proximate to the outlet. In some embodiments, systems and methods of the disclosure employ a filter proximate to or at the outlet Examples of filters that may be used include, but are not limited, to ultrafilters, nanofilters, any hollow fiber filter, flat filters, and membrane filters. Unlike the membranes between the first and second chambers, in some embodiments, the filters of the present disclosure may be designed to capture or trap live bacterial cells in the fluid or retentate of the second chamber. Such fluid may be accessed by the outlet and either drained, syphoned or aspirated from the second chamber for further analysis using the steps disclosed herein.

After separating one or a plurality of bacterial pathogens from a sample by drawing the motile pathogens from the first chamber to the second chamber, analysis on the separated bacterial cells may be performed to confirm the presence, absence or quantity of bacterial cells in the sample. Analysis steps may include one or a combination of the following steps: concentrating a solution comprising the bacterial pathogens, performing microscopy to observe and count the number of bacterials cells, plating and/or culturing the bacterial pathogens, determining cell number by operating an automatic cell counter, or performing a series of polymerase chain reactions (PCR) experiments. In still other embodiments, exemplary alternative measurement or analysis steps are radioimmunoassay (RIA) tests, immunofluorescent assay (IFA) tests, enzyme immunoassay (EIA or ELISA) tests, DNA probing methods. Other known commercial methods for analysis of separated bacterial pathogens include the following techniques in Table 2.

TABLE 2

Partial list of commercially-available, nucleic acid-based assays used in the detection of bacterial pathogens*

| Organism | Trade Name | Format | Manufacturer |
|---|---|---|---|
| Clostridium botulinum | Probelia | PCR | BioControl |
| Campylobacter | AccuProbe | probe | GEN-PROBE |
|  | GENE-TRAK | probe | Neogen |
| Escherichia coli | GENE-TRAK | probe | Neogen |
| E. coli O157:H7 | BAX | PCR$_a$ | Qualicon |
|  | Probelia | PCR | BioControl |
| Listeria | GENE-TRAK$_c$ | probe | Neogen |
|  | AccuProbe | probe | GEN-PROBE |
|  | BAX | PCR | Qualicon |
|  | Probelia | PCR | BioControl |
| Salmonella | GENE-TRAK$_c$ | probe | Neogen |
|  | BAX | PCR | Qualicon |
|  | BIND$_b$ | phage | BioControl |
|  | Probelia | PCR | BioControl |
| Staphylococcus aureus | AccuProbe | probe | GEN-PROBE |
|  | GENE-TRAK | probe | Neogen |
| Yersinia enterocolitica | GENE-TRAK | probe | Neogen |

*Table modified from: Feng, P., App. I, FDA Bacteriological Analytical Manual, 8A ed.
$_a$Polymerase chain reaction
NOTE:
This table is intended for general reference only and lists known available methods. Presence on this list does not indicate verification, endorsement, or approval by FDA for use in food analysis.

Still other techniques that may be employed to detect the presence, absence or quantity of bacterial pathogens include the following in Table 3:

TABLE 3

Partial list of commercially-available, antibody-based assays for the detection of foodborne pathogens and toxins

| Organism/toxin | Trade Name | Assay Format$^a$ | Manufacturer |
|---|---|---|---|
| Bacillus cereus diarrhoeal toxin | TECRA | ELISA | TECRA |
|  | BCET | RPLA | Unipath |
| Campylobacter | Campyslide | LA | Becton Dickinson |
|  | Meritec-campy | LA | Meridian |
|  | MicroScreen | LA | Mercia |
|  | VIDAS | ELFA$^b$ | bioMerieux |
|  | EiaFOSS | ELISA$^b$ | Foss |
|  | TECRA | ELISA | TECRA |
| Clostridium botulinum toxin | ELCA | ELISA | Elcatech |
| C. perfringens enterotoxin | PET | RPLA | Unipath |
| Escherichia coli |  |  |  |
| EHEC**$^c$ O157:H7 | RIM | LA | REMEL |
|  | E. coli O157 | LA | Unipath |
|  | Prolex | LA | PRO-LAB |
|  | Ecolex O157 | LA | Orion Diagnostica |
|  | Wellcolex O157 | LA | Murex |
|  | E. coli O157 | LA | TechLab |
|  | O157&H7 | Sera | Difco |
|  | PetrifilmHEC | Ab-blot | 3M |
|  | EZ COLI | Tube-EIA | Difco |
|  | Dynabeads | Ab-beads | Dynal |
|  | EHEC-TEK | ELISA | Organon-Teknika |
|  | Assurance$^e$ | ELISA | BioControl |
|  | HECO157 | ELISA | 3M Canada |

TABLE 3-continued

Partial list of commercially-available, antibody-based assays for the detection of foodborne pathogens and toxins

| Organism/toxin | Trade Name | Assay Format$^a$ | Manufacturer |
|---|---|---|---|
|  | TECRA | ELISA | TECRA |
|  | E. coli O157 | ELISA | LMD Lab |
|  | Premier O157 | ELISA | Meridian |
|  | E. coli O157:H7 | ELISA | Binax |
|  | E. coli Rapitest | ELISA | Microgen |
|  | Transia Card E. coli O157 | ELISA | Diffchamb |
|  | E. coli O157 | EIA/capture | TECRA |
|  | VIP$^e$ | Ab-ppt | BioControl |
|  | Reveal | Ab-ppt | Neogen |
|  | Quix Rapid O157 | Ab-ppt | Universal HealthWatch |
|  | ImmunoCardSTAT | Ab-ppt | Meridian |
|  | VIDAS | ELFA$^b$ | bioMerieux |
|  | EiaFOSS | ELISA$^b$ | Foss |
| Shiga toxin (Stx) | VEROTEST | ELISA | MicroCarb |
|  | Premier EHEC | ELISA | Meridian |
|  | Verotox-F | RPLA | Denka Seiken |
| ETEC$^c$ |  |  |  |
| Labile toxin (LT) | VET-RPLA | RPLA | Oxoid |
| Stabile toxin (ST) | E. coli ST | ELISA | Oxoid |
| Listeria | Microscreen | LA | Microgen |
|  | Listeria Latex | LA | Microgen |
|  | Listeria-TEK$^e$ | ELISA | Organon Teknika |
|  | TECRA$^e$ | ELISA | TECRA |
|  | Assurance$^e$ | ELISA | BioControl |
|  | Transia Plate Listeria | ELISA | Diffchamb |
|  | Pathalert | ELISA | Merck |
|  | Listertest | Ab-beads | VICAM |
|  | Dynabeads | Ab-beads | Dynal |
|  | VIP$^e$ | Ab-ppt | BioControl |
|  | Clearview | Ab-ppt | Unipath |
|  | RAPIDTEST | Ab-ppt | Unipath |
|  | VIDAS$^e$ | ELFA$^b$ | bioMerieux |
|  | EiaFOSS | ELISA$^b$ | Foss |
|  | UNIQUE | Capture-EIA | TECRA |
| Salmonella | Bactigen | LA | Wampole Labs |
|  | Spectate | LA | Rhone-Poulenc |
|  | Microscreen | LA | Mercia |
|  | Wellcolex | LA | Laboratoire Wellcome |
|  | Serobact | LA | REMEL |
|  | RAPIDTEST | LA | Unipath |
|  | Dynabeads | Ab-beads | Dynal |
|  | Screen | Ab-beads | VICAM |
|  | CHECKPOINT | Ab-blot | KPL |
|  | 1-2 Test$^e$ | diffusion | BioControl |
|  | SalmonellaTEK$^e$ | ELISA | Organon Teknika |
|  | TECRA$^e$ | ELISA | TECRA |
|  | EQUATE | ELISA | Binax |
|  | BacTrace | ELISA | KPL |
|  | LOCATE | ELISA | Rhone-Poulenc |
|  | Assurance$^e$ | ELISA | BioControl |
|  | Salmonella | ELISA | GEM Biomedical |
|  | Transia Plate Salmonella Gold | ELISA | Diffchamb |
|  | Bioline | ELISA | Bioline |
|  | VIDAS$^e$ | ELFA$^b$ | bioMerieux |
|  | OPUS | ELISA$^b$ | TECRA |
|  | PATH-STIK | Ab-ppt | LUMAC |
|  | Reveal | Ab-ppt | Neogen |
|  | Clearview | Ab-ppt | Unipath |
|  | UNIQUE$^e$ | Capture-EIA | TECRA |
| Shigella | Bactigen | LA | Wampole Labs |
|  | Wellcolex |  | Laboratoire Wellcome |

TABLE 3-continued

Partial list of commercially-available, antibody-based assays for the detection of foodborne pathogens and toxins

| Organism/toxin | Trade Name | Assay Format[a] | Manufacturer |
|---|---|---|---|
| Staphylococcus aureus | Staphyloslide | LA | Becton Dickinson |
|  | AureusTest[e] | LA | Trisum |
|  | Staph Latex | LA | Difco |
|  | S. aureus VIA | ELISA | TECRA |
| enterotoxin | SET-EIA | ELISA | Toxin Technology |
|  | SET-RPLA | RPLA | Unipath |
|  | TECRA[e] | ELISA | TECRA |
|  | Transia Plate SE | ELISA | Diffchamb |
|  | RIDASCREEN | ELISA | R-Biopharm |
|  | VIDAS | ELFA[b] | bioMerieux |
|  | OPUS | ELISA[b] | TECRA |
| Vibrio cholera | choleraSMART | Ab-ppt | New Horizon |
|  | bengalSMART | Ab-ppt | New Horizon |
|  | choleraScreen | Agglutination | New Horizon |
|  | bengalScreen | Agglutination | New Horizon |
| enterotoxin | VET-RPLA[d] | RPLA | Unipath |

*Table modified from: Feng, P., App. I, FDA Bacteriological Analytical Manual, 8A ed.
[a]Abbreviations: ELISA, enzyme linked immunosorbent assay; ELFA, enzyme linked fluorescent assay; RPLA, reverse passive latex agglutination; LA, latex agglutination; Ab-ppt, immunoprecipitation.
[b]Automated ELISA
[c]EHEC—Enterohemorrhagic E. coli; ETEC—enterotoxigenic E. coli
[d]Also detects E. coli LT enterotoxin
[e]Adopted AOAC Official First or Final Action Antibodies may be used in conjunction with the analysis step or as part of the device, for example, in the case of an immunfluorscent antibody present in the buffer solution comprising the chemoattractant in the second chamber. In other embodiments, the device, system and methods are free of antibodies or methods of steps using antibodies.

In some embodiments, sample liquid is pre-filtered prior to concentration. Examples of filters that may be used include, but are not limited to, plastic mesh, metallic mesh, plastic screens, metallic screens, bed filters, media-type filters, bag filters, and flat filters.

The system or device may also have one or a plurality of Examples of the fittings that may be used include, but are not limited to, plastic, stainless steel, copper, brass, and Teflon® coated.

Examples of pumps that may be used include, but are not limited to, syringe pumps, double diaphragm pumps, single diaphragm pumps, solenoid pumps, gear pumps, and centrifugal pumps.

Examples of valves that may be used include, but are not limited to, solenoid valves, ball valves, air-operated valves, elliptic valves, diaphragm valves, metering valves, needle valves, butterfly valves, and check valves.

Examples of gases used to displace liquid in the permeate space, include, but are not limited to, compressed air, nitrogen, argon, oxygen, hydrogen, helium, and xenon. Gas pressures used should not to exceed the pressure which will damage the membrane. In some embodiments, compressed air is used at a pressure between about 1 psi to 80 psi. In some embodiments, compressed air is used at a pressure between 25 psi to 45 psi. In some embodiments, an atmospheric drain is used. In some embodiments, compressed air is used to displace liquid in the permeate space for about 1 second to 30 seconds or more.

The present disclosure also provides for systems and methods that determine whether a sample is contaminated. The methods comprise separating one or a plurality of bacterial cells (of one or a plurality of species) from the sample and then performing any one or plurality of analysis steps disclosed herein. One of ordinary skill in the art can utilize currently published government standards to compare analysis results and determine if the presence or quantity of bacterial cells in a sample correlates to a contamination event. In some embodiments, the devices, systems, and methods provided herein comprise determining whether a sample is contaminated by comparing the quantitative data from any of the above-mentioned analysis methods to the standards set forth in Table 4.

TABLE 4

Bacterial Contamination Performance Standards of the US government.

*Salmonella* Performance Standards for Ground Beef

| Product class | Pathogen | Performance standard | Number of samples tested | Sampling Method | Maximum number of positives to achieve standard | Revised Standard Implemented |
|---|---|---|---|---|---|---|
| Ground Beef | Salmonella | 7.5% | 53 | One sample per event | 5 | N/A |

*Salmonella/Campylobacter* Performance Standards for Poultry

| Product | Maximum Acceptable % Positive | | Performance Standard | |
|---|---|---|---|---|
|  | Salmonella | Campylobacter | Salmonella | Campylobacter |
| Broiler Carcasses^ | 7.5 | 10.4 | 5 of 51 | 8 of 51 |
| Turkey Carcasses^ | 1.7 | 0.79 | 4 of 56 | 3 of 56 |
| Comminuted Chicken* | 25.0 | 1.9 | 13 of 52 | 1 of 52 |

TABLE 4-continued

Bacterial Contamination Performance Standards of the US government.

| Comminuted Turkey* | 13.5 | 1.9 | 7 of 52 | 1 of 52 |
|---|---|---|---|---|
| Chicken Parts* | 15.4 | 7.7 | 8 of 52 | 4 of 52 |

~The maximum percent positive for *Salmonella* and *Campylobacter* under the performance standards for young chicken and turkey carcasses is listed in FSIS Directive 10,250.1
*Developed proposed performance standards published in the FRN Docket No. FSIS-2014-0023

Kits

In some embodiments, kits in accordance with the present disclosure may be used to isolate various strains of bacteria from simple (bacteria only) or complex (food, blood, feces, etc.) samples. In some embodiments, kits for isolating bacteria comprise any of the devices described above and optionally further comprise various types of buffers, chemoattractants, and chemorepellents. Any array, system, or component thereof disclosed may be arranged in a kit either individually or in combination with any other array, system, or component thereof. The disclosure provides a kit to perform any of the methods described herein. In some embodiments, the kit comprises at least one container comprising one or a plurality of buffers, chemoattractants, and/or chemorepellents. In some embodiments, the kit comprises at least one container comprising any of the chemoattractants and/or chemorepellents described herein. In some embodiments, the chemoattractants and/or chemorepellents are in solution (such as a buffer with adequate pH and/or other necessary additive to minimize degradation of the chemoattractant(s) and/or chemorepellent(s) during prolonged storage). In some embodiments, the chemoattractants and/or chemorepellents are lyophilized for the purposes of resuspension after prolonged storage. In some embodiments, the chemoattractants and/or chemorepellents are suspended in a gel or hydrogel. In some embodiments, the kit optionally comprises instructions to perform any or all steps of any method described herein. In some embodiments, the kit comprises an array or system described herein and instructions for implementing one or a plurality of steps using any computer program product disclosed herein. It is understood that one or a plurality of the steps from any of the methods described herein can be performed by accessing a computer program product encoded on computer storage medium directly through one or more computer processors or remotely through one or more computer processors via an internet connection or other virtual connection to the one or more computer processors. In some embodiments, the kit comprises a computer-program product described herein or requisite information to access a computer processor comprising the computer program product encoded on computer storage medium remotely. In some embodiments, the computer program product, when executed by a user, calculates the quantity of bacteria in a solution sample, normalizes one or more bacteria counts, generates one or more bacterial profiles, and/or displays any of the bacteria counts and/or bacterial profiles to a user. In some embodiments, the kit comprises a computer program product encoded on a computer-readable storage medium that comprises instructions for performing any of the steps of the methods described herein. In some embodiments, the invention relates to a kit comprising instructions for providing one or more bacteria counts, one or more normalized bacteria counts, one or more bacteria profiles, or any combination thereof. In some embodiments, the kit comprises a computer program product encoded on a computer storage medium that when, executed on one or a plurality of computer processors, quantifies and/or displays a bacteria count, determines a bacteria profile, and/or any combination thereof. In some embodiments, the kit comprises a computer program product encoded on a computer storage medium that, when executed by one or a plurality of computer processors, quantifies bacterial counts of one or more simple or complex samples. In some embodiments, kit comprises instructions for accessing the computer storage medium, quantifying bacterial counts normalizing bacterial counts, determining a bacterial profile of a sample, and/or any combination of steps thereof. In some embodiments, the computer-readable storage medium comprises instructions for performing any of the methods described herein. In some embodiments, the kit comprises an array or system disclosed herein and a computer program product encoded on computer storage medium that, when executed, performs any of the method steps disclosed herein individually or in combination and provides instructions for performing any of the same steps.

The disclosure further provides for a kit comprising one or a plurality of containers that comprise one or a plurality of the buffers, chemoattractants, and/or chemorepellents disclosed herein. In some embodiments, the kit comprises: any device disclosed herein, any buffer media disclosed herein, any chemoattractant disclosed here, and chemorepellent disclosed herein, and/or a computer program product disclosed herein optionally comprising instructions to perform any one or more steps of any method disclosed herein. In some embodiments, the kit does not comprise cell media.

The kit may contain two or more containers, packs, or dispensers together with instructions for preparation of an device. In some embodiments, the kit comprises at least one container comprising any device or system described herein and a second container comprising a means for maintenance, use, and/or storage of any device. In some embodiments, the kit comprises a composition comprising any buffer, chemoattractant(s), and/or chemorepellent(s) disclosed herein in solution or lyophilized or dried and accompanied by a rehydration mixture or in a gel or hydrogel. In some embodiments, the buffers, chemoattractant(s), and/or chemorepellent(s) and rehydration mixture may be in one or more additional containers.

The compositions included in the kit may be supplied in containers of any sort such that the shelf-life of the different components are preserved, and are not adsorbed or altered by the materials of the container. For example, suitable containers include simple bottles that may be fabricated from glass, organic polymers, such as polycarbonate, polystyrene, polypropylene, polyethylene, ceramic, metal or any other material typically employed to hold reagents or food; envelopes, that may consist of foil-lined interiors, such as aluminum or an alloy. Other containers include test tubes, vials, flasks, and syringes. The containers may have two compartments that are separated by a readily removable membrane that upon removal permits the components of the compositions to mix. Removable membranes may be glass, plastic, rubber, or other inert material.

Kits may also be supplied with instructional materials. Instructions may be printed on paper or other substrates, and/or may be supplied as an electronic-readable medium, such as a floppy disc, CD-ROM, DVD-ROM, zip disc, videotape, audio tape, or other readable memory storage device. Detailed instructions may not be physically associated with the kit; instead, a user may be directed to an internet web site specified by the manufacturer or distributor of the kit, or supplied as electronic mail.

The disclosure also provides a kit comprising: a first container comprising: (i) a first frame defining a compartment configured to receive one or a plurality of samples; (ii) a second frame defining a second compartment at least partially filled with a buffer and/or chemoattractant; and (iii) a membrane positioned therebetween.

The disclosure also provides a kit comprising: a first container comprising: (i) a first frame defining a compartment configured to receive one or a plurality of samples; (ii) a second frame defining a second compartment configured for receiving a buffer and/or chemoattractant; and (iii) a membrane positioned therebetween; and a second container comprising a buffer and/or chemoattractant.

EXAMPLES

Example 1: Embodiment Build

Chip Building:

The device was fabricated using two pieces of Polycarbonate milled with a CNC MDX 540. The membranes used were nucleopore track-etched membranes with pore size of about from about 5 microns to about 50 microns. PCT20047100 (I also tried other pore sizes from 50 micron size pores to 5 microns size pores). The membranes were assembled according to FIG. 11. Access holes to the chambers were drilled with a 1.2 mm diameter drill bit. Luer blunt needles (gauge 19) were inserted in the holes, and glued using epoxy for one minute.

Experiments:

All the fluidic inlets commercial luerlock plugs were used to close all the fluidic inlets/outlets of the device (6: 2 for the extraction chamber, 2 for the sample chamber and 2 for the repellent chamber).

The gasket between the two parts of the chip was fabricated by laser cutting PDMS sheets (1.5 mm thick). The two parts of the chip were bond together using a laser-cut ring of Double sided tape (#96042, 3M, 130 µm thickness)

Loading the Extraction Chamber:

The luerlock plugs were removed from the extraction chamber, and a 5 ml BD plastic syringe was used to load 3 ml of chemotaxis buffer. The chemotaxis buffer, contained phosphate buffer (pH 7.0; 10-2 M) and potassium ethilenediaminetetracetate (EDTA; 10-4 M). Alternatively we also used Tryptone broth with similar results. After the chamber was loaded, we disconnected the syringe, and placed again the luerlock plugs in the inlet and outlet of the extraction chamber.

Loading the Sample Chamber:

The luerlock plugs were removed from the sample chamber, and the food sample was introduced through the inlet with a 5 ml BD plastic syringe.

In one case the food sample was ground meat (80% lean) purchased in a grocery store diluted in 1:1 in tryptone broth containing 10^6 bacteria per ml (*Salmonella Typhimurium* or *E. coli* 0157H7) in mid exponential growth, total volume 1.5 ml. The sample was pressed through a metallic food-mill with pores about 0.8 mm to reduce the size of the meat chunks so that everything could flow through the blunt needle gauge 19.

In another case a sample of cow manure was diluted 1:1 in tap water. The sample was placed in a filter-bag to remove large pieces of hay, and then 1.5 ml of the sample was introduced in the device After the chamber was loaded, we disconnected the syringe, and placed again the luerlock plugs in the inlet and outlet of the sample chamber.

Loading the repellent chamber: The luerlock plugs were removed from the repellent chamber, and the repellent solution (20% Ethanol diluted in distilled water, total volume 3 ml) was introduced through the inlet with a 5 ml BD plastic syringe. After the chamber was loaded, we disconnected the syringe, and placed again the luerlock plugs in the inlet and outlet of the repellent chamber.

Experiment. The whole device was placed on top of a hot plate at about 30 degrees Celsius, and let sit for about 30 min.

Recovering the bacteria. The luerlock plugs were removed only from the extraction chamber, and a 5 ml BD plastic syringe was used extract the liquid contents from the chamber. The solution from the extraction or receiving chamber was plated in selective agar plates or inspected using a cell cytometer (cellometer) using an inverted Zeiss microscope. Control experiments were performed with the samples without inoculating pathogenic bacteria. Cell number and efficiency of bacterial cell detection were calculated by: (i) in respect to cell number, average population estimates were determining by counting live bacterial cells under the microscopic field and the multiplying the number of living cells with the estimated total surface area of the microscopic field; and (ii) in respect to efficiency, by dividing the population values estimated by microscopic field essitmations by the total number of bacterial cells counted in the matrix at the beginning of the experiments. In some experimental section runs, we were able to observe over 75% of the live bacterial cells from the first chamber migrate and become separated in the second chamber.

Example 2

FIG. 1 depicts a concept diagram of bacterial separation using chemotaxis. The core principle of bacterial separation using chemotaxis is that bacteria will self-separate from non-bacterial elements of a complex sample in the presence of chemoattractants, which they will move towards, or chemorepellents, which they will move away from. In the depicted example, contaminated lettuce is ground up and introduced into one opening of a microfluidic chip. A concentrated chemorepellent is introduced into a second opening of the chip, creating a chemical gradient. When bacteria from the food sample reach the chemical gradient, they actively move away from the chemorepellent, leaving the non-bacterial portion of the food sample behind. The bacteria are then extracted from a third opening, where they are effectively recovered in a clean solution for further analysis.

Figure 2A:
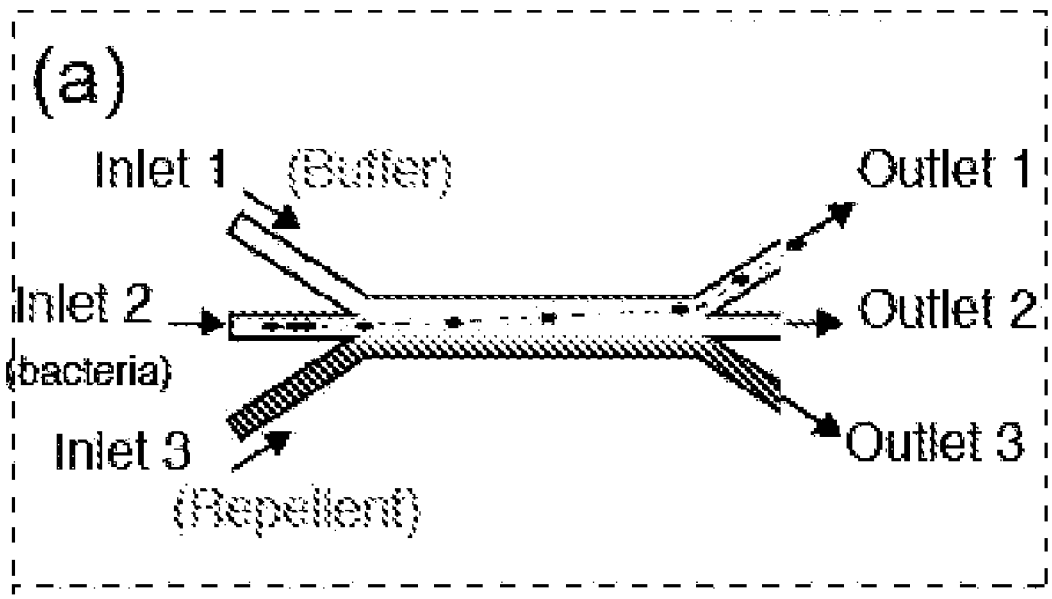
FIGS. 2A, 2B, 2C, and 2D depict diagrams of and data from a microfluidic device use to study bacterial chemotaxis.
Figure 2B:
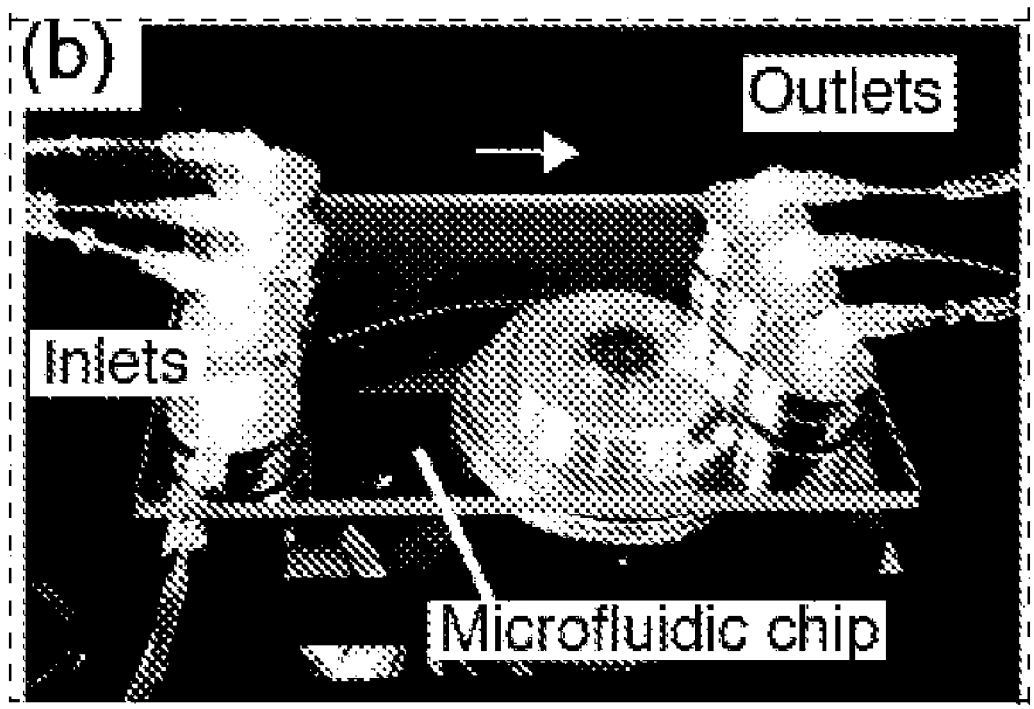
Figure 2C:
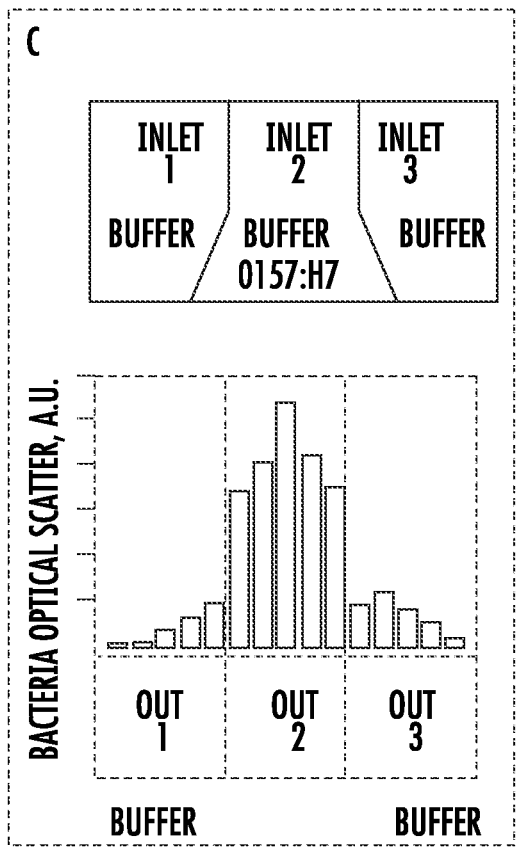
Figure 2D:
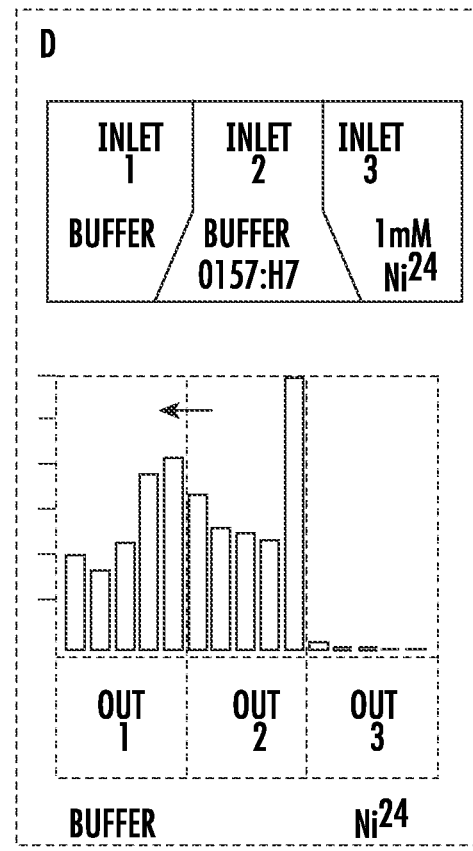

Example 3—Embodiments Free of Fluid Flow Except in Connection with Filling One or More Chambers One way to create a microfluidic chip in which to cause bacterial chemotaxis is through active fluid-flow through a chip, substantial planar surface with a microfluidic channel that is in fluid communication with one or more chambers that comprise one or a plurality of chemorepellents and/or chemoattractants. In FIG. 2A, a microfluidic chip is diagramed where fluid flows from inlets on the left to outlets on the right. In the depicted example, a bacterial sample is placed in the middle inlet 2, while a buffer is placed in the top inlet 1 and a chemorepellent is placed in the bottom inlet 3. The three streams merge into a main channel, resulting in a chemical gradient of chemorepellent perpendicular to the direction of the fluid-flow. Bacteria swim away from the chemorepellent, and can be recovered on the further outlet from the chemorepellent. FIG. 2B shows a picture of such a device. FIGS. 2C and 2D depict experimental data of a control test and a test with 1 mM N+ as a chemorepellent, respectively. In FIG. 2C, the bacterial population, is highest in outlet 2, indicating that bacteria moved little in relation to their insertion point of inlet 2. In FIG. 2D, bacteria are recovered in equal amount in outlets 1 and 2, with almost no bacteria being recovered in outlet 3. This shows how the bacteria moved away from the chemorepellent inserted in inlet 3

While active fluid-flow microfluidic chips work on a basic level, the shape of the chemical gradient, and therefore the bacterial separation, greatly depends on the total flow rates through the chip. Additionally, fluid velocity can differ in the middle of the device than at the walls, the ability of the bacteria to switch from streams is heterogeneous. Additionally, fluid-flow devices will have difficulty working with fluids of different viscosity (e.g. ethanol mixtures and buffer), because differences in viscosity changes the width of the streams in the main channel, and thus it modifies the flow at the outlets. This is crucial, since the goal is to separate bacteria from complex samples with very different fluidic properties (e.g. food wash from crop material, or blood).

Figure 3A:
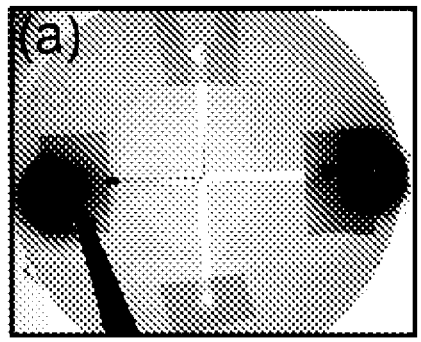
Figure 3B:
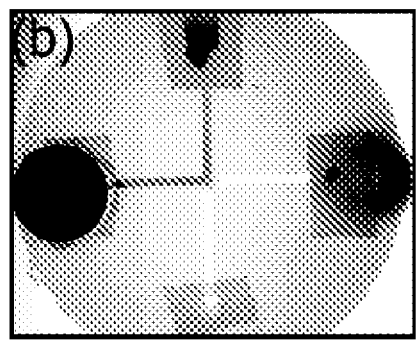
Figure 3C:
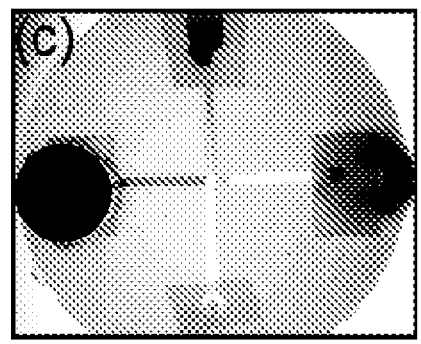
Figure 3D:
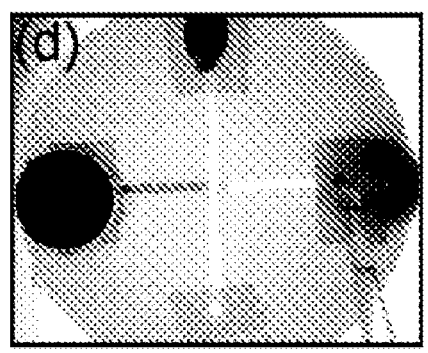
Figure 3E:
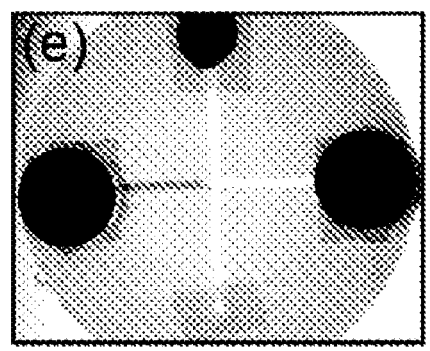
Figure 3I:
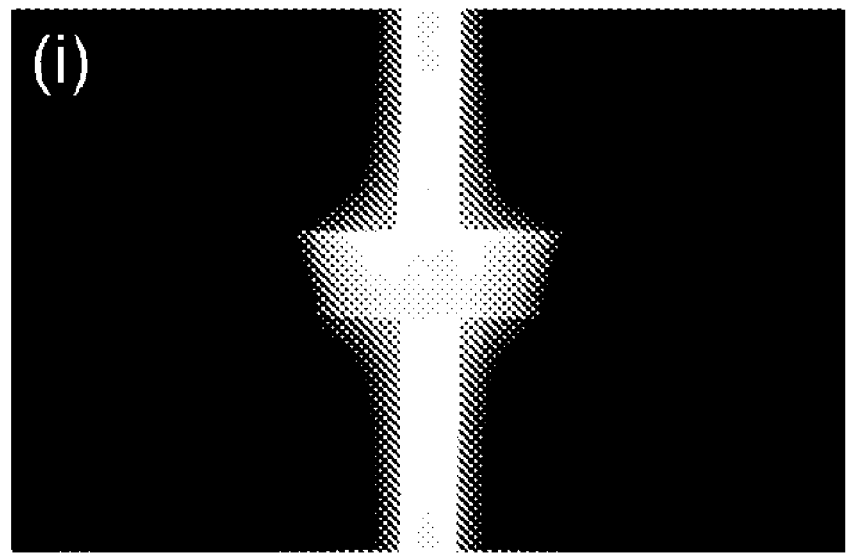
Figure 3J:
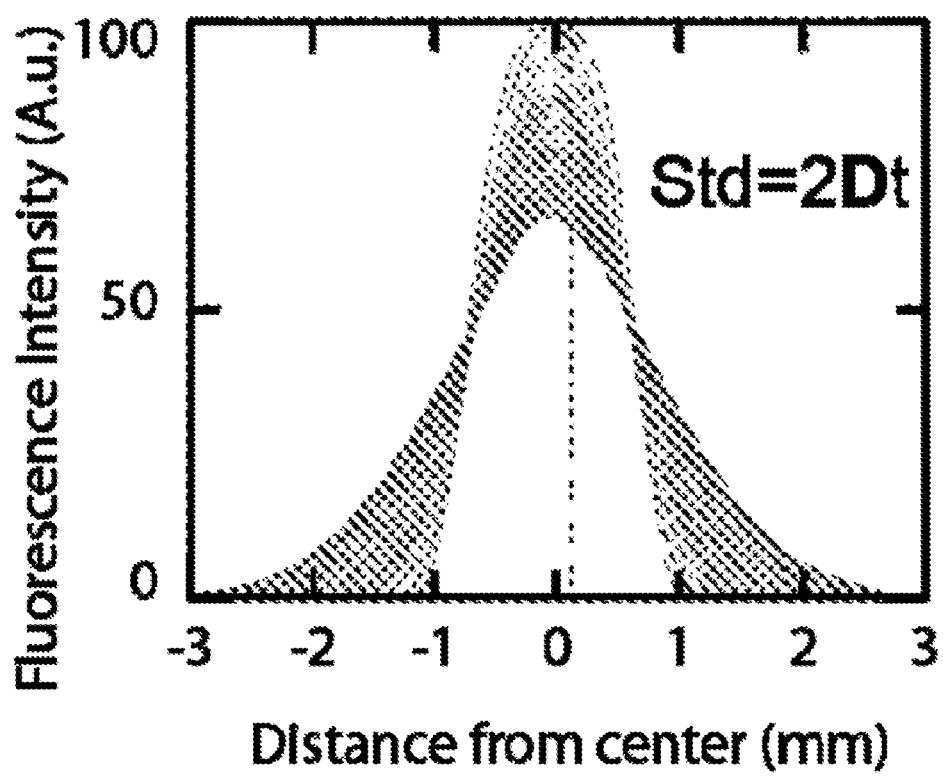

Another way to create a microfluidic chip in which to cause bacterial chemotaxis is to create chemical gradients based on diffusion instead of active fluid-flow. In such a device, the chemicals and bacteria samples are introduced into the device by simple pipetting. The chip has two crossing channels, one to set up the chemical gradient and the other one to introduce bacteria in a complex sample. The chemical gradient is introduced as small droplet through the horizontal channel and its inlet is sealed with a magnetic plug to prevent fluid movement. FIGS. 3A, 3B, 3C, 3D, and 3E depict the addition of dye and buffer to the device to study their diffusion. Initially the two channels are filled with buffer. In FIG. 3A, dye is introduced through inlet 1 (left) and then in FIG. 3B that inlet is sealed with a plug. In FIG. 3C, buffer is introduced through inlet 2 (top) to clean the vertical channel. In FIG. 3D, inlet 3 (right) is cleaned with buffer, and then sealed with a plug in FIG. 3E. FIGS. 3F and 3G depict the evolution of the chemical gradient at the channel intersections of the device. FIG. 3H depicts a graph of the temporal evolution of the chemical gradient. The experiment was reproduced three times, and gradient shows to be reproducible and predictable. In FIG. 3I, fluorescein was introduced though inlet 2 (top), where a complex sample with bacteria should be introduced normally, to verify the absence of fluid-flow. FIG. 3J depicts a graph of the distribution of fluorescein over time. The distribution changes as a Gaussian distribution, which changes in time with a standard deviation of 2Dt, with D being the diffusion coefficient of fluorescein and t being time. The concentration profile depicted agrees with values reported for fluorescein, demonstrating that the gradients are purely diffusive and predictable.

Figure 4:
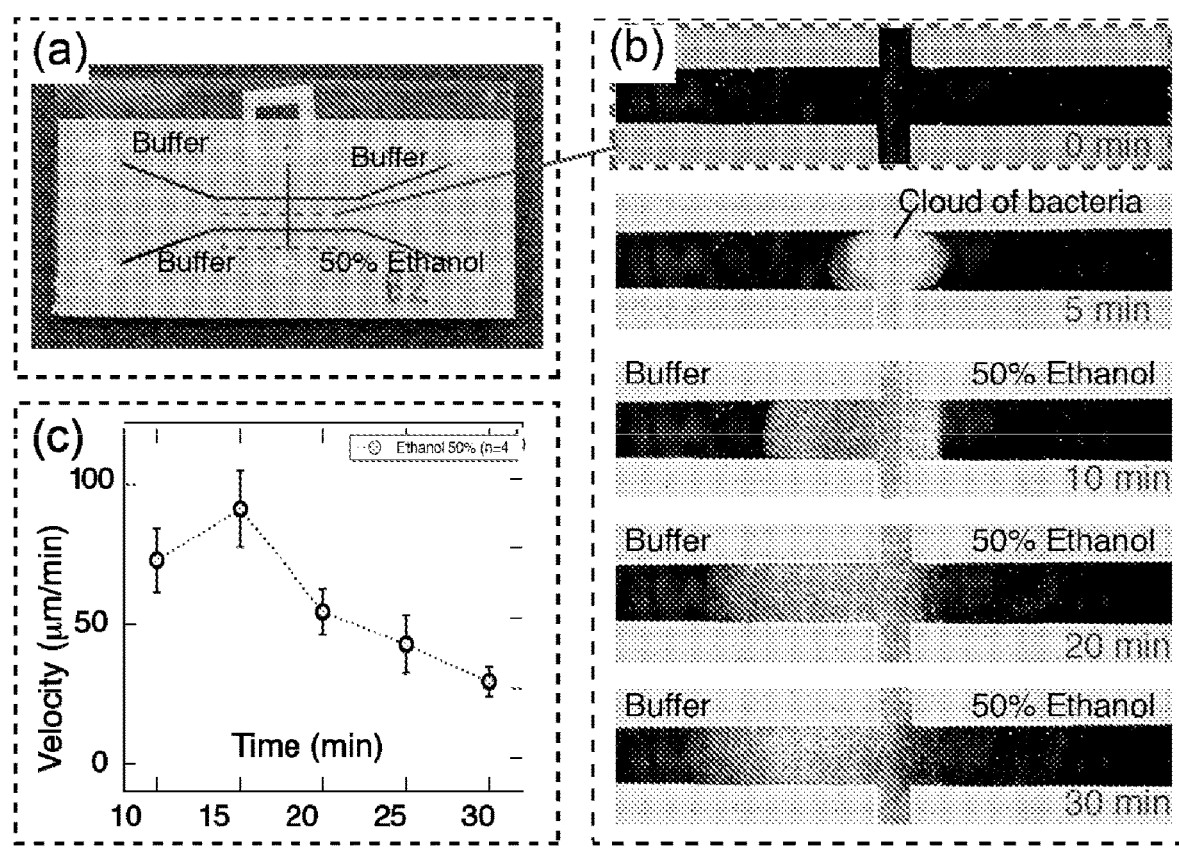
FIGS. 4A, 4B, and 4C depict bacterial separation from a complex sample using chemotaxis.

Having shown that chemical gradients based on diffusion are possible in a microfluidic chip using sample dyes, the next step is to separate actual bacteria. In FIGS. 4A, 4B, and 4C, chemorepellents are used, the logic being that it may be difficult to lure bacteria using chemoattractants, as bacteria should have nutrients (themselves chemoattractants) in a real complex sample. FIG. 4A depicts a diagram of the device, which has two parallel, horizontal channels one for the chemorepellent gradient and a second for a buffer control, and one vertical channel for the introduction of bacteria. The chemorepellent is 50% ethanol, and the bacteria are unspecific, being grown from dirt in LB broth for 8 hours at 30 degrees centigrade in an incubator-shaker. FIG. 4B depicts only the chemorepellent channel over time. At time 0 minutes, the ethanol was introduced in the horizontal channel. At time 5 minutes the bacteria sample was introduced through the vertical channel. Bacteria next to the maximum concentration of ethanol became non-motile and putatively dead. Over time, the bacteria are clearly seen moving away from the ethanol. The velocity drift of the median of the bacterial distribution away from the ethanol gradient is shown in FIG. 4C.

Example 4—Embodiment with Multiple Chemotactic Gradients

Figure 5A:
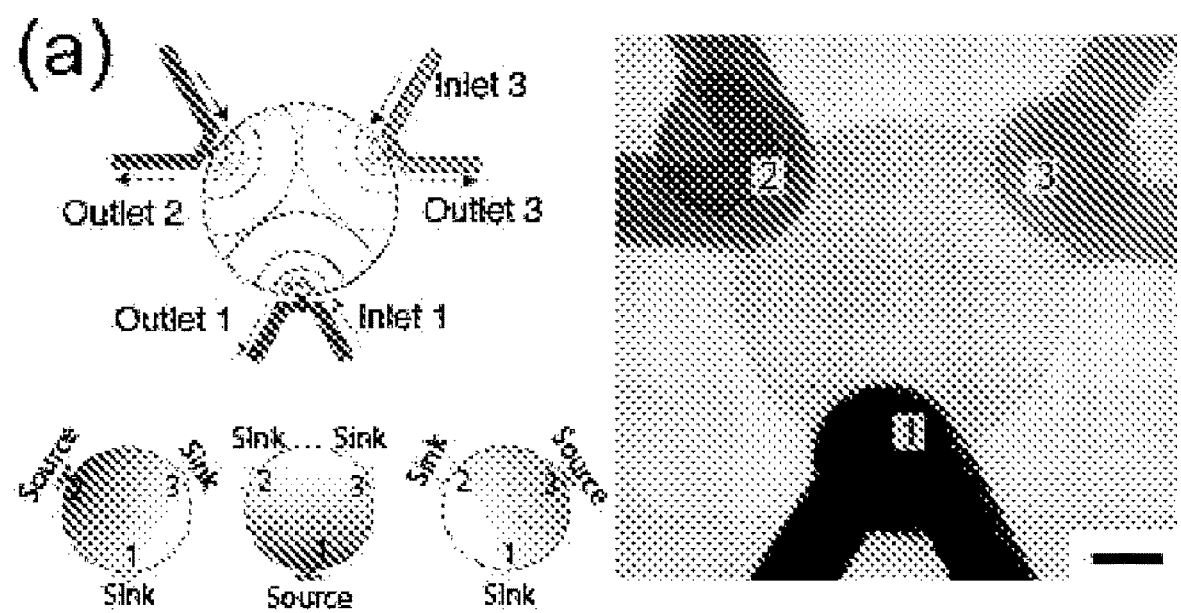
FIGS. 5A and 5B depict a diagram of and data from a device that generates diffusive, overlapping, chemotaxis gradients.
Figure 5B:
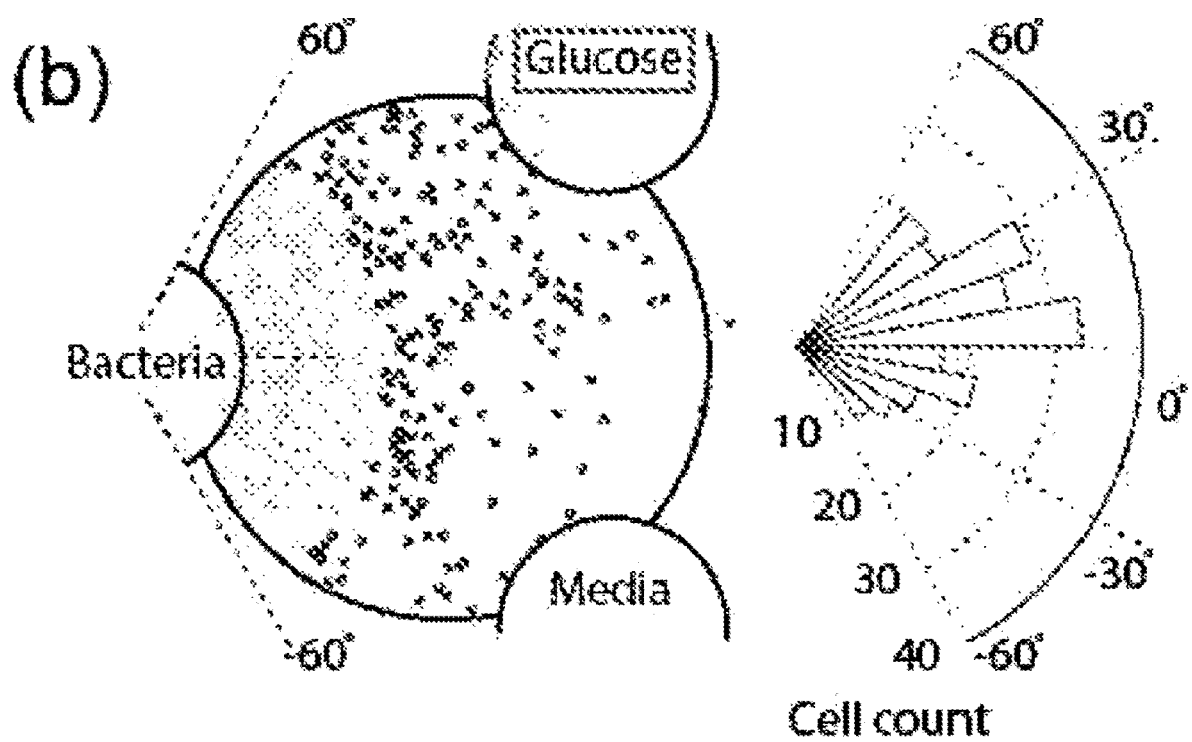

Having demonstrated the concept of separating bacteria in a linear chemical gradient, it is possible to create a microfluidic device that generates multiple diffusive, overlapping chemical gradients for the purpose of separating different species and strains of bacteria by their differential chemotactic behavior. FIG. 5A depicts a device that has three inlets arranged at equal points around a circular central chamber. The outlets are close to each inlet, and a variety of chemical gradients can be created in the central chamber depending on what combination of buffers and chemicals are placed in each inlet. FIG. 5B depicts data showing the movement of bacteria placed in one inlet moving preferentially towards glucose, a chemoattractant for bacteria such as *Salmonella typhumurium* and *Pseudomonas aeruginosa*. The microfluidic device depicted here can accommodate more than three chemical sources, and can be used to study bacterial responses in combinatorial gradients.

Figure 6A:
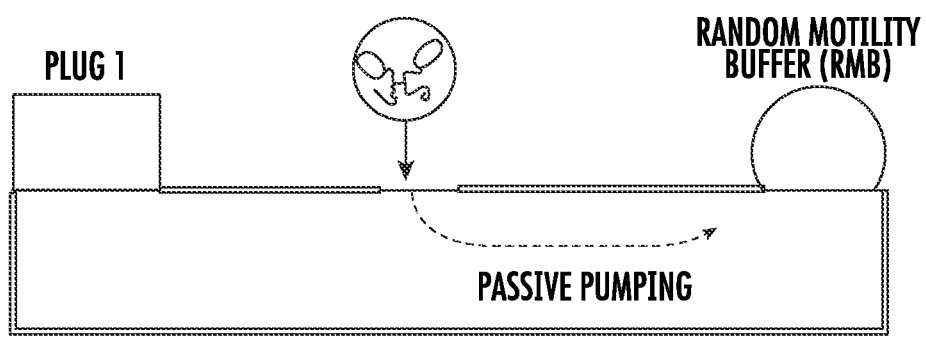
FIGS. 6A, 6B, and 6C depict a schematic of the parallelization of a chemotaxis gradient separation.
Figure 6B:
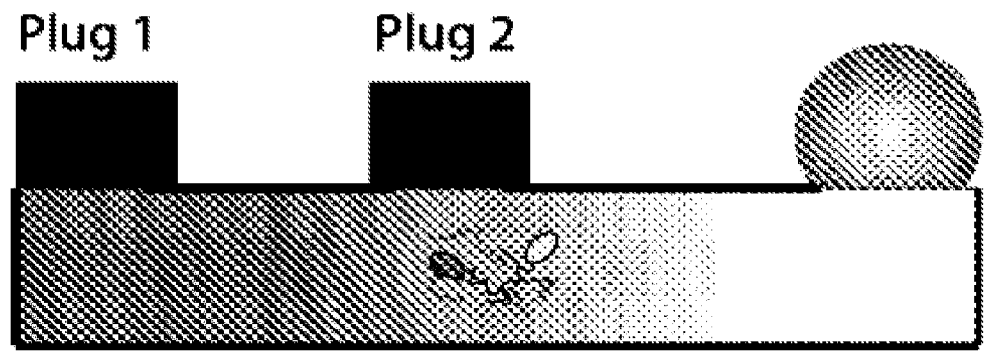
Figure 6C:
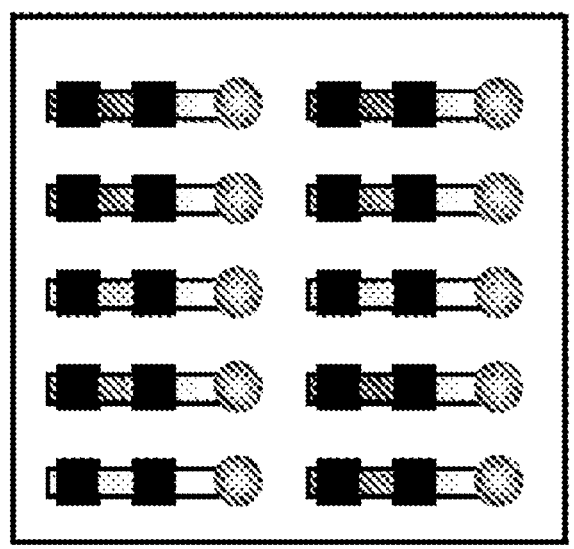

In moving towards better designs for microfluidic devices, certain concepts should be addressed. The first of these is the goal of a simplest device possible that allows for high throughput screening of bacterial chemotaxis. Specifically, finding the minimal dimension needed to perform bacterial separation is ideal, as is the ability to perform simultaneous or otherwise rapid experiments in a high-throughput format. In FIG. 6A, a schematic is shown where a sample is introduced using passive pumping in the center of a pre-existing chemical gradient. Once the bacterial inlet is plugged as shown in FIG. 6B, the bacteria in the sample are free to move along the gradient, in this case away from the chemorepellent introduced near plug 1 and towards the open buffer inlet (with the bead of liquid shown instead of a plug). Since bacterial displacement is proportional to distance, finding the minimal dimensions required for chemotaxis to dominate is important to reduce the overall footprint of a device. Smaller sizes can also result in parallelization of the chemotaxis assay, for example, having multiple gradient chambers on one larger chip as shown in FIG. 6C.

Figure 7A:
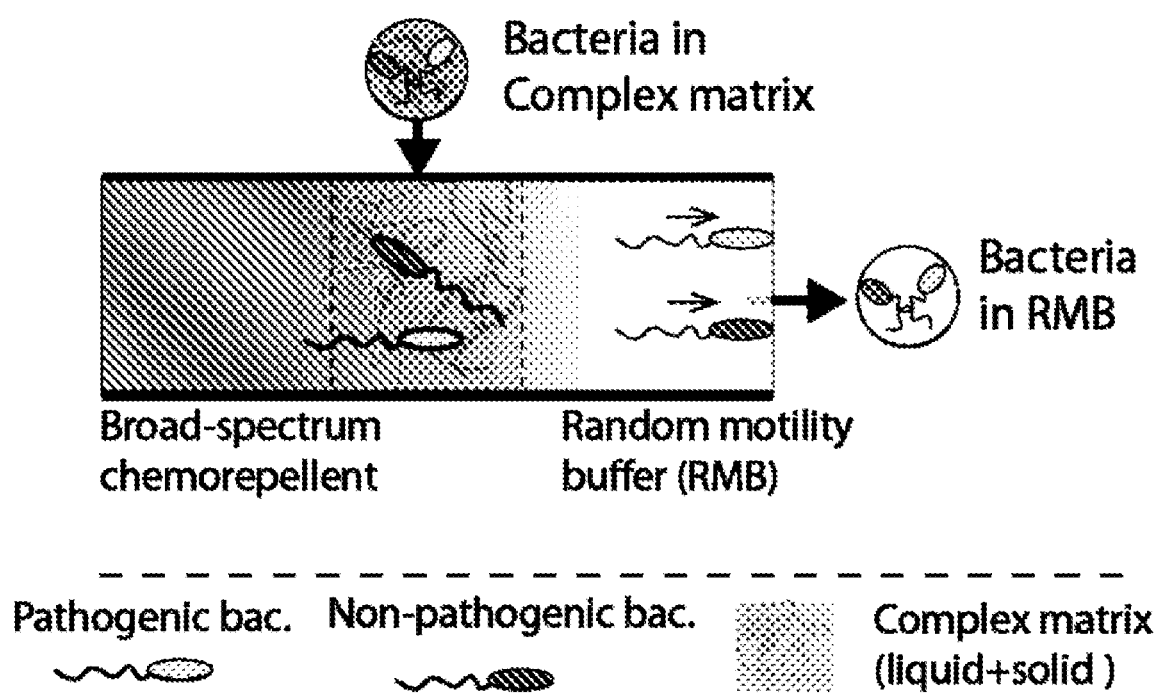
FIGS. 7A, 7B, 7C, and 7D depict the study of bacterial separation from a complex matrix.
Figure 7B:
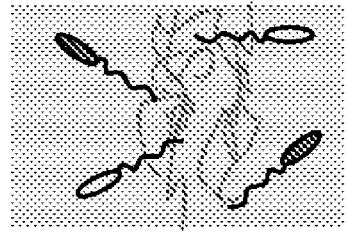
Figure 7C:
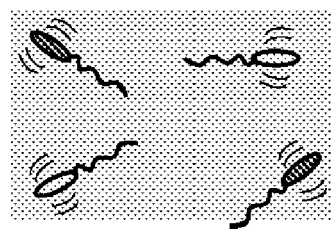
Figure 7D:
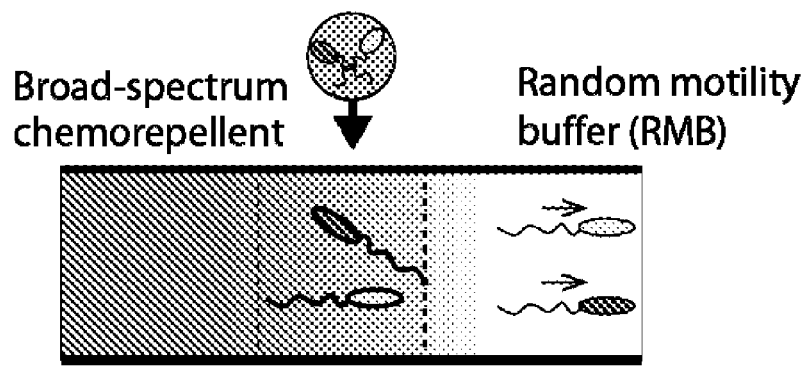

The second concept to be addressed is how the bacteria themselves react in a complex sample such as food product or blood, when that complex sample is exposed to a chemical gradient. FIG. 7A depicts the goal: the separating of all bacteria, pathogenic and non-pathogenic, from a complex matrix using a chemical gradient. Problems could arise with types of bacteria being non-motile in real-life complex matrixes, or being unable to properly detach from larger particles to move down the chemical gradient. FIG. 7B depicts this concept as a diagram of the adherence and release of bacterial cells from solids in complex samples. An example of this is enterohemorrhagic *E. coli* bacteria, which utilize flagella to move and adhere to niches in the intestinal track, but subsequently get rid of them to escape the immune system. The distribution of flagellated and un-flagellated bacteria in contaminated food has not currently been studied. Another specific issue is the actual motility of certain bacterial strains. FIG. 7C depicts this concept as a diagram of the random motility of bacteria. An example of this *Salmonella Typhumurium*, which is highly motile even in the upper side of its growth curve, versus *E. coli*, which is motile only on the exponential section of its growth curve. Additionally, certain compounds are known to promote motility, including auto-inducer-1, auto-inducer-2, short-chain fatty acids, and different chemorepellents, as is optimization of temperature for many bacterial species. Finally, certain types of chemorepellents are lethal to bacteria, or may significantly harm their motility. Also of note is that although bacteria flee from harmful compounds and swim toward nutrients, this is not an absolute rule. FIG. 7D depicts this concept as a diagram of separating pathogenic and non-pathogenic bacteria from a complex sample. It has been demonstrated that E. coli escapes from compounds that do not affect their viability and proliferation and swim towards chemical that they cannot metabolize. Many types of chemoattractants and chemorepellents should be utilized, and several are listed on Table 1.

TABLE 1

Types of chemoattractants and chemorepellents

| | Chemoattractant | Chemorepellent |
| --- | --- | --- |
| Acetate | *C. vinosum* | *E. coli, S. typhimurium* |
| Aspartate | *E. coli, S. typhimurium* | *P. fluorescencens* |
| Benzoate | *P. putida* | *E. coli, S. typhimurium* |
| Leucine | *B. subtilis* | *E. coli, S. typhimurium* |
| Phenol | *E. coli* | *S. typhimurium* |
| Tryptophan | *B. subtilis, C. vinosum* | *E. coli, S. typhimurium* |
| Valine | *B. subtilis* | *E. coli, S. typhimurium* |
| $H^+$, $OH^-$ | *R. sphaeroids* | *E. coli, C. vinosum* |
| Citrate | *S. typhimurium* | (no effect on *E. coli*) |
| Maltose | *E. coli* | (no effect on *S. typhimurium*) |
| $Co^{2+}$, $Ni^2$ | (no effect on *S. typhimurium*) | *E. coli* |
| glucose | *S. typhumurium, P. aeruginosa* | *E. coli* |

Example 5—Selective Chemoattractants

Figure 8A:
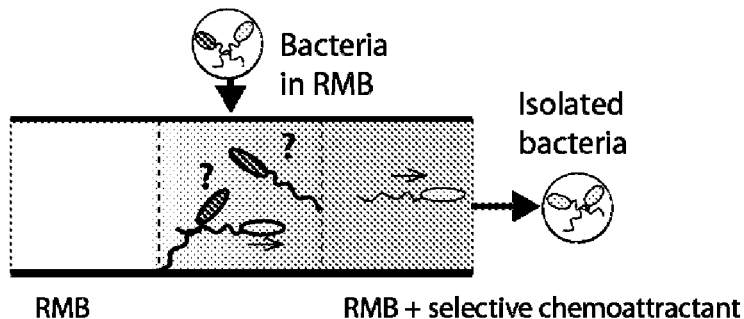
FIGS. 8A, 8B, and 8C depict the study of separating different bacterial species using selective chemoattractants and/or chemorepellents.
Figure 8B:
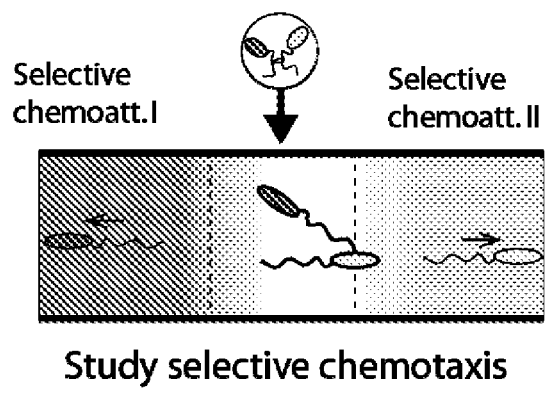
Figure 8C:
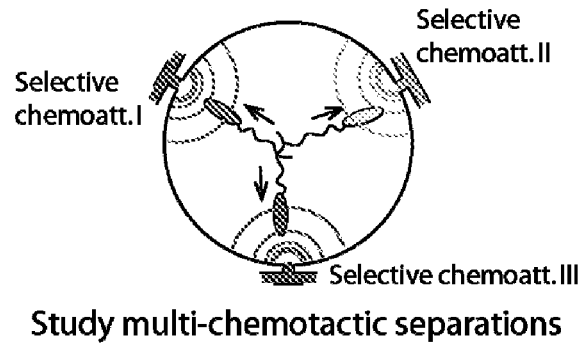

The third concept to be addressed is separating different bacterial species using selective chemoattractants. Closely related to the concept of separating pathogenic and non-pathogenic bacteria described previously, the goal is to find optimal combinations of chemoattractants and chemorepellents to perform faster and highly specific separations. FIG. 8A depicts an example where one type of bacteria is isolated from a mixture of different types of bacteria due to a selective response to a chemoattractant. FIG. 8B depicts an example where different types of bacteria are separately isolated from a complex mixture due to the use of different selective chemoattractants in a linear gradient. Even different strains within bacterial species may also have different chemotactic responses to optimize their survival and proliferation in their native microenvironment. Different bacterial strains usual share the same types of receptors, so this differential chemotactic response among strains might be existent but significantly subtler. Recent observations that *E. coli* strains isolated from the feces from carnivores preferred aspartate to serine, while strains isolated from herbivores were attracted to both chemicals equally or preferred serine to aspartate. Additionally, it is a common practice to sensitize a bacterial strain to a non-preferred nutrient before analyzing its chemotactic response to the compound. For example, galactose is not metabolized by *E. coli* if glucose is present. Thus, to study chemotaxis towards galactose it is required to wash and incubate the *E. coli* in minimal media with galactose for 1 hour. Then the bacteria are washed again, resuspended in motility buffer and exposed to a galactose gradient. Since in most cases protein degradation in *E. coli* is done by dilution (cell doubling) rather than enzymatic activity, this bacterial adaptation may last for multiple generations. Thus it is possible to study the chemotactic separation of bacterial strains sensitized to their environmental niches, as might be the case in contaminated complex samples. This idea can be expanded beyond linear chemical gradients, and FIG. 8C depicts the separation of three types of bacteria using three chemoattractants in a complex chemical gradient.

One way to address these concepts involves the separation of bacteria from non-bacterial particles in a complex sample, and the use of different chemical gradients. We sought to incorporate membranes into a microfluidic device. Semipermeable membranes with pore diameters large enough for bacteria to pass through are capable of isolating chambers in a device, such that fluid flow between chamber would be eliminated, but chemical gradients created by diffusion would be allowed to form. If a complex sample where introduced into a first chamber isolated by a membrane, bacteria would be free to migrate into another chamber by passing through the membrane, while larger and/or non-motile particles from the complex sample would remain in the first chamber. If the microfluidic device had multiple chambers separated by one or more membranes, a variety of chemical gradients could be established by diffusion in a relatively compact space.

Figure 9A:
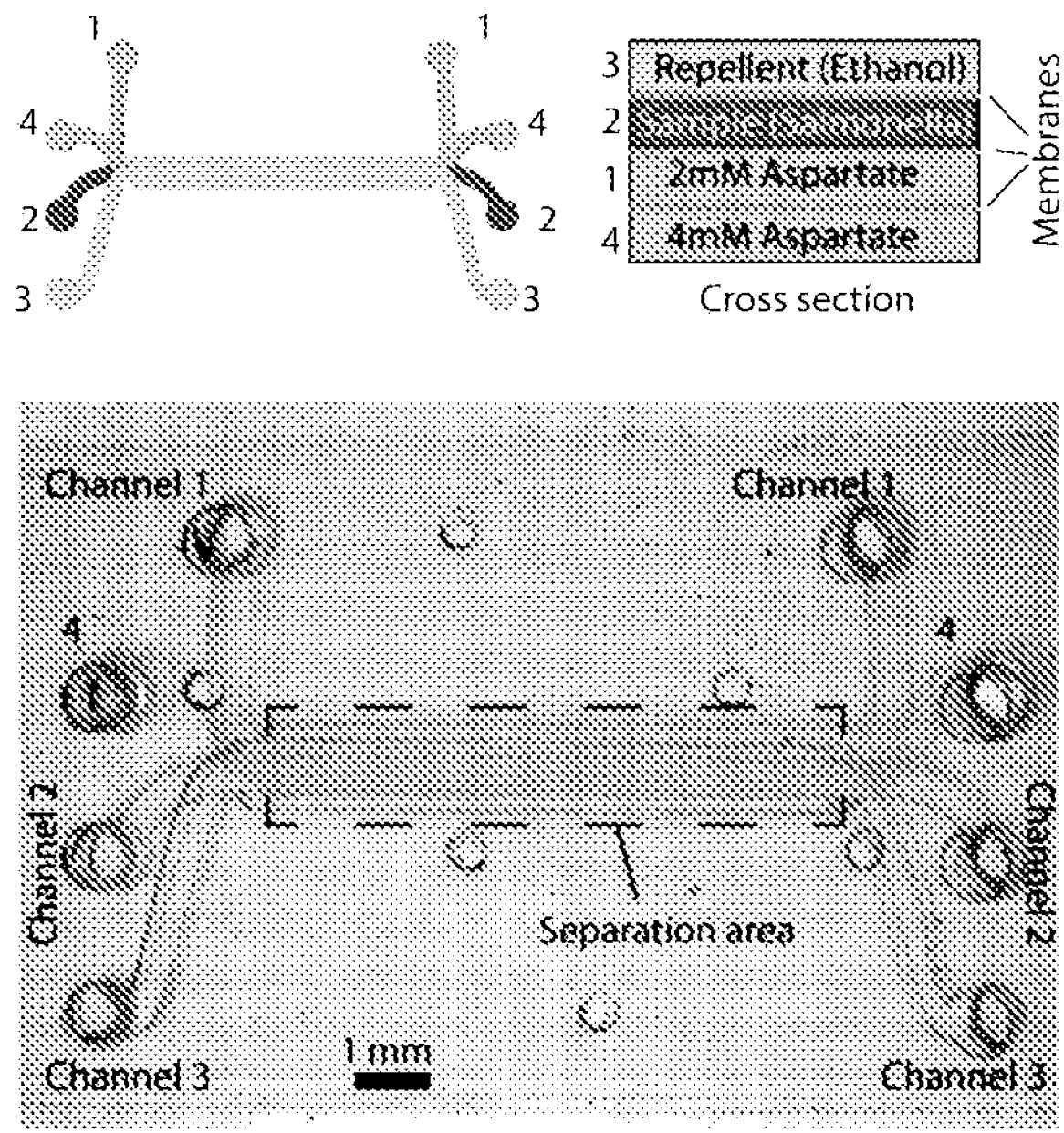
FIGS. 9A and 9B depict a diagram of and data from a device that generates diffusive chemotaxis gradients.
Figure 9B:
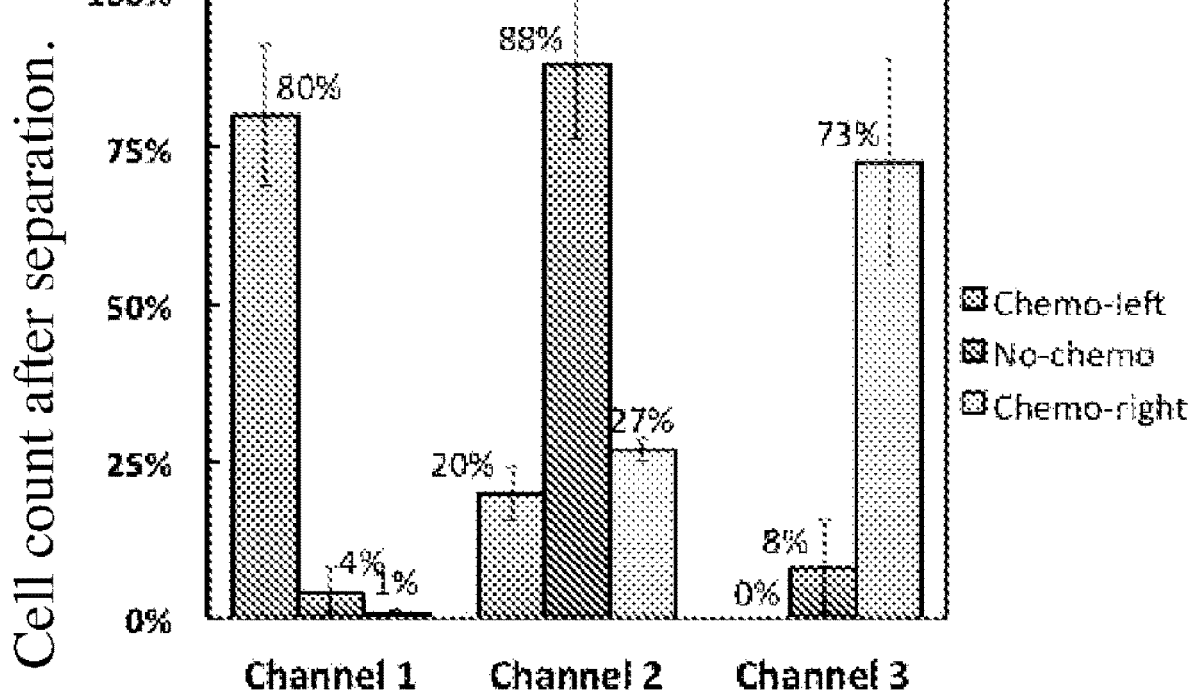

FIG. 9A depicts a diagram of a microfluidic chip with four channels that overlap in the vertical direction, with each channel being separated by a semipermeable membrane. Each channel has an inlet/outlet on either end of the chip, each channel can be filled using regular pipettes. The four channels overlap in the vertical direction to maximize contact are amongst channels and optimizes the time required for the chemical gradients to form. The membranes between the channels prevent fluid flow while allowing the chemical gradients to form and bacteria to migrate between the channels. FIG. 9B shows the separation and isolation of *S. typhimurium* using the chemoattractant aspartate. 2 mM α-methyl aspartate was introduced through channel 1, a concentration of *S. typhimurium* was introduced through channel 2, and a buffer through channel 3. The contents of each channel was extracted after approximately 30 minutes and the bacterial density measured using a cell counter (left hand bar in each column). The results demonstrate that most bacteria crossed over to the channel containing maximal concentration of chemoattractant. To control for the potential effects of gravity, the experiments were repeated with buffer and chemoattractant introduced through the opposite channels, and the results were the same (right hand bar in each column). Control experiments were also performed to evaluate random dispersion of bacteria to channels 1 and 3 filled with buffer; very few of the bacteria moved away from channel 2 without the present of the chemoattractant (middle bars in each column). These results validate the approach of leveraging chemotaxis in the presence of semipermeable membranes as a rapid way to isolate bacteria from complex samples.

The use of semipermeable membranes also has another advantage: the reintroduction of fluid-flow to the microfluidic device. While the problems with conventional microfluidic devices using fluid-flow throughout the device has been previous described, the use of membranes between channels allows for fluid-flow in one chamber, while the remaining chambers are passive gradients only. For example, pumping fluid continuously in and out of the chamber designed to recover bacteria allows for the counting of bacterial that crosses the membrane as a function of time. It is also possible to change or alter the concentration of a chemoattractant over time to improve separation. Additionally, a magnetic stirrer can be added to the recovery chamber to prevent static build-up immediately next to the membrane, or to homogenize the chemical concentration. A magnetic stirrer in one chamber does not create fluid-flow across membranes.

Figure 10A:
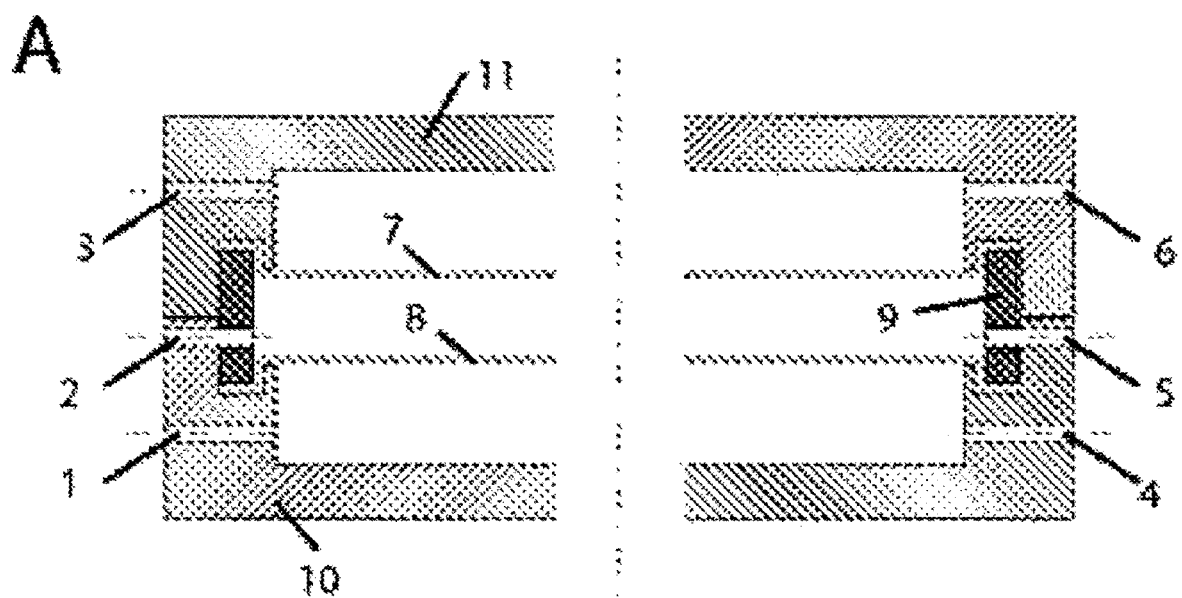
FIGS. 10A, 10B, 10C, and 10D depict a diagram of a three chambered microfluidic device.
Figure 10B:
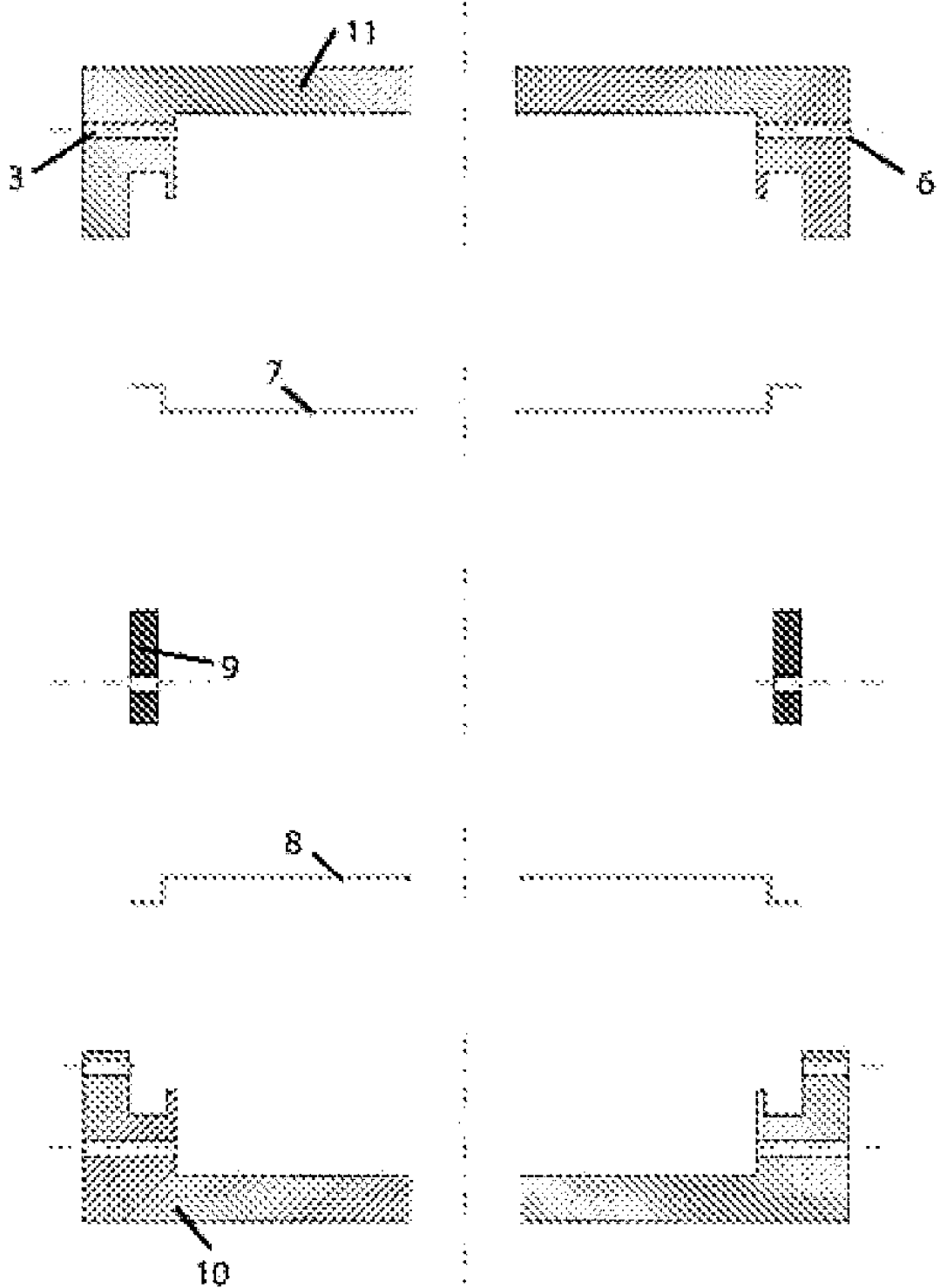
Figure 10C:
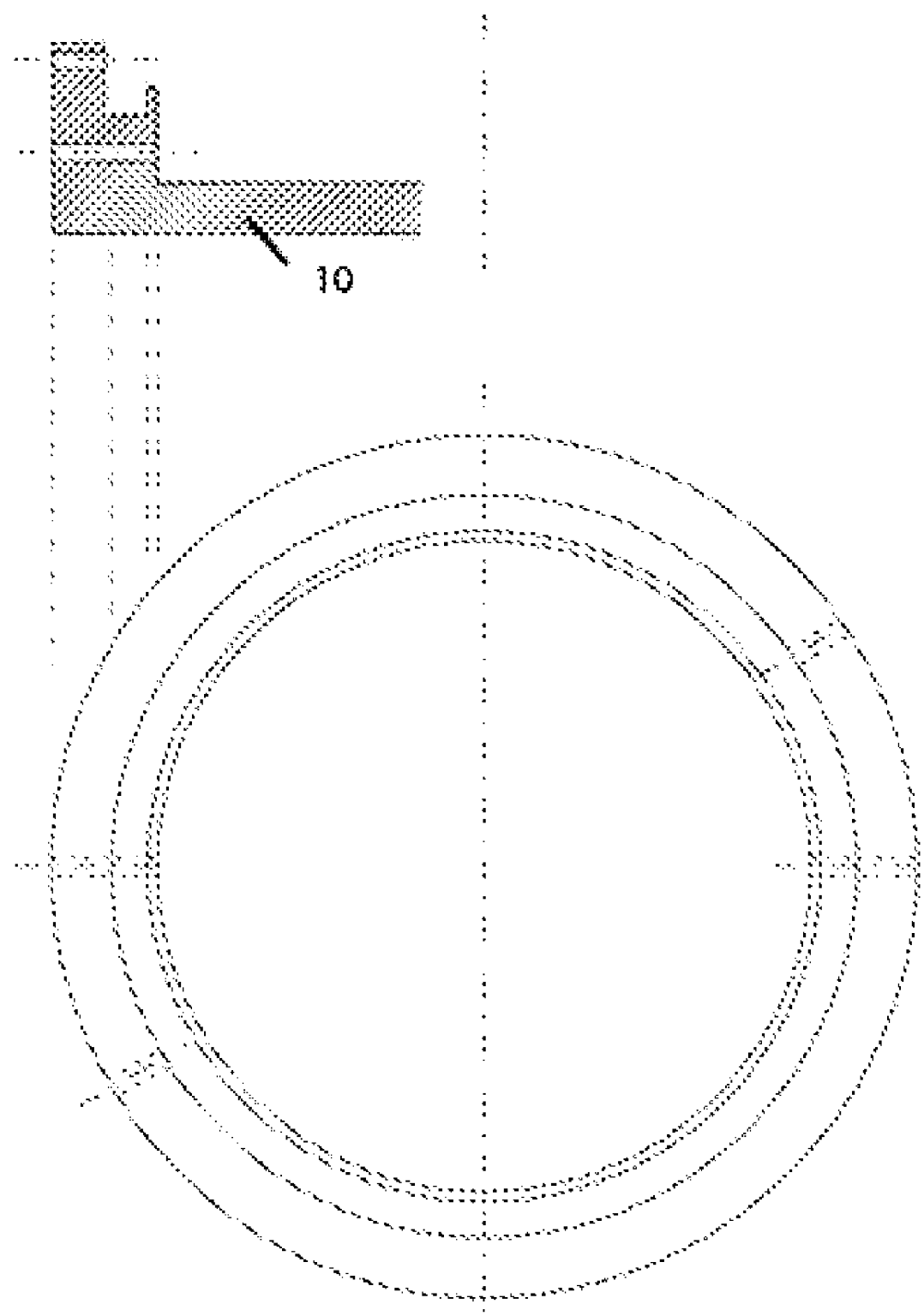
Figure 10D:
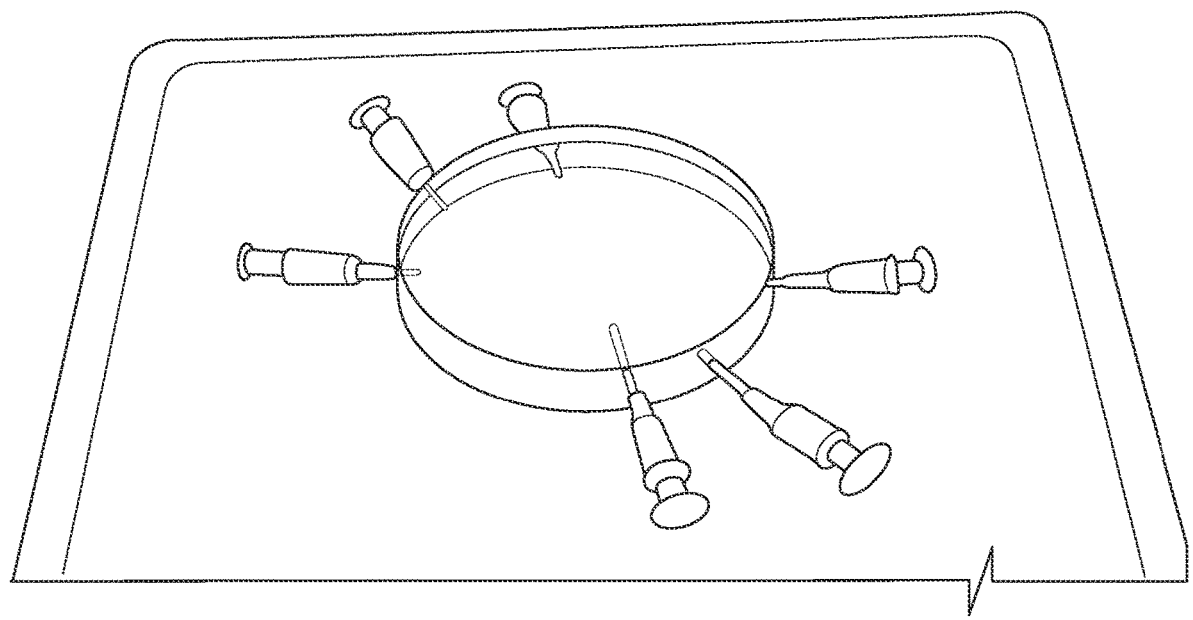

FIG. 10A depicts a diagram of a cross section of a microfluidic device with three chambers isolated by two membranes. Inlet 1 is paired with outlet 4; inlet 2 is paired with outlet 5, and inlet 3 is paired with outlet 6. The middle chamber is for the introduction of sample, while the upper and lower chambers are for the introduction of chemoattractant or chemorepellent, and after separation, for the extraction of bacteria. A magnetic stirrer can be placed in the bottom chamber, and spun with a standard magnetic stir plate. FIG. 10B depicts a diagram of a cross section of the device where each element is separated for clarity. The membranes 7 and 8 are held in place between two plastic frames 10 and 11 with a rubber gasket 9. The depicted device is circular, as shown in FIG. 10C. FIG. 10D depicts a picture of the assembled device. The attached ports allow for easy insertion and extraction of liquid, chemicals, or sample without disturbing the device, with for instance a needle and syringe.

As sample of data from use of the device follow:

|  |  |  |  | Meat diluted 1:1 | Meat diluted 1:2 | Meat diluted 1:3 |
|---|---|---|---|---|---|---|
| *E. coli* O157H7 in 1.5 ml device | Eth20%/GroundMeat + O157H7/Media | 30 min | E: | 77.60% | 109.80% | 57.00% |
| *S. Typhimurium* in 1.5 ml device | Eth20%/Media + *Salmonella*/Media | 25 min | E: | 76.4% + −8% |  |  |
|  | Eth20%/Media + *Salmonella*/Media | 30 min | E: | 87.9% + −7% |  |  |

"Eth" = Ethanol.
'E" = extraction efficiency and the calculation based upon estimated number of live bacterial cells in the second chamber after 30 mins. divided by the number of live bacterial cells observed before introduction of the sample into the device. Extraction efficiencies were shown to be from about 57% to about 100%.

The volume of the first chamber (sample chamber) was 1.5 mL.

Example 6—Disposable Commercial Device

The disposable device will have three components.
(1) The receiving or isolation chamber will be fabricated in plastic by injection molding as disclosed in Example 1. The receiving chamber will be constructed in a cylindrical form with an opening at one end of the cylinder. A thin membrane of about 1 mm in width will be adhered to the top of the cylinder with a lip of plastic that forms a ledge or ridge of plastic on one side of the plastic or indentation around an internal portion of the perimeter of the plastic. The membrane will be used as or top portion of the chamber. This first chamber will have one fluidic inlet and one fluidic outlet that is incorporated in the plastic sides of the chamber. The receiving chamber will be packaged independently and will be pre-filled with a chemotactic buffer or fluid with specific chemo-attractants and/or specific chemo-repellents in a range of serial dilutions from about 1 mM to about 100 mM. The cheomtatctic buffer may be in the form of a soft gel (e.g. <0.3% agar concentration), which is incorporated into the chamber by heating and liquefying the agar solution prior to addition of the filling the chamber. In order to prevent the liquid to leak out of the chamber through the membrane, a plastic lid softly adhered to the membrane is present and will be removed from it by the final operator to start the experiment.

(2) The second part will be a plastic ring that will be fitted on top of the membrane in the aforementioned part (1). The ring will have an inner diameter that will match the active area of the membrane. The height of the ring (in the direction parallel to the rotational axis of symmetry) will be at least 1 mm, and it could have any dimension from about 1 mm to about 6 mm. The operator will fill the space inside the ring with a food sample up to the upper surface of the ring. This second component may be packaged together in a container of a kit with the first component.

(3) The third component of the kit will be a slab of semisolid material such as a 4% agar gel containing a specific chemorepellent from about 1 mM to about 100 mM concentration. Instead of a semisolid agar it maybe a material that can hold liquid and allow diffusion of molecules such a sponge. The third component to be packaged independently in a sealed plastic or metallic container. The final operator will open the container remove the slab and place it on top of the second component (2) and the food sample. Individual slabs of agar comprising the Most probably this component of the kit will be made with various chemorepellents that are bacteria-specific, and thus, the operator will use different bacteria-specific slabs of agar depending on the assay.

This third part may have layers within the semisolid agar to "program" the diffusion of different chemicals in time. For example, slow diffusing chemicals may be placed in a layer closer to the area that will be in contact with the food sample, and faster diffusing molecules may be placed in layers farther away from the area that will be in contact with the food sample. The different layers may contain at least one membrane to provide consistency to the slab, and also to control the flux rate of molecules between layers. Each layer may be packaged independently, or with plastic tabs to prevent diffusion of molecules between layers prior to the experiment. The tabs will be removed before the experiment starts. Optimization of these embodiment will be performed with two or three chemorepellents and two or three chemoattractants disclosed in Table 1 with serial concentrations between 1 mM and 100 mM of the chemoeffector. If ethanol is used at a chemorepellent, the ethanol solution will be used at a final concentration of about 20% EtOH suspended in deionized water or salt buffer.

Detection:

Once the separation is done, the liquid in the extraction chamber will be removed through the outlet, if the extraction is bacteria specific, counting the number of bacteria will provide a first indication for contamination. The liquid with the bacteria will be automatically passed through a membrane with pore size <1 µm, typically 0.4 µm. the membrane area will be small (<3 mm in diameter). Buffer will be passed through the membrane to remove any molecules present at the membrane's surface while the bacteria will be held by the pores. The DNA will be extracted from the bacteria at the membrane, and will be automatically used for PCR detection.

Example 6 "Stamp" Embodiment (Prophetic)

In this embodiment two gels "sandwich" a the food sample. There is no need for plastic chamber one of the gels has one membrane with small pores to allow bacteria to cross. In this case the membrane does not need to be mechanically stretched. The food sample will be stamped on top of the gel with the membrane, and the second gel with chemorepellent will be placed on top. After 30 min-1 h only the gel below the membrane is recovered. The gel can then be melted and the bacteria extracted, or the gel can have selective nutrients with colorimetric readout for the presence of the pathogen after incubation. The assembly and distance between the gels will be preserved by adding individual "spacers " into the food sample, or by "laminating" the food sample and the gels with mechanical rods or mechanical planes that "sandwich" the layers in the order of the depicted layers.

Example 7—Microfluidic Device Assembly

FIGS. 11A through 11I depict the side view of a device depicted in FIG. 10. The dashed line refers to a line of symmetrically down a center axis of the device. The purpose of the line is to depict a cylindrically shaped object from a side perspective and convey the mirrored aspect of this embodiment.

Figure 11A:
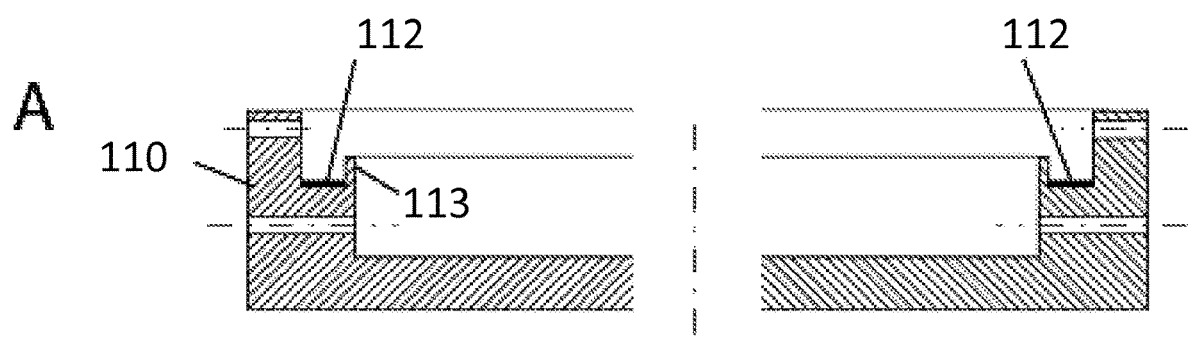
FIGS. 11A through 11I depict a side view of a cylindrically shaped embodiment with subpanels depicting the manufacture of the embodiment and method of affixing a membrane of the disclosure between the first and second chambers. This figure also depicts the steps necessary to tighten the membrane between the first and second chamber.

FIG 11A 110 is the same sidewalls of the sample chamber as the one described in FIG. 10. The only addition is 112, which is double sided tape 120 µm thick in the form of a ring placed within a ridge 113 that runs along one internal perimeter of the sample chamber. The tape 112 is adhered to 110 as shown in the picture.

Figure 11B:
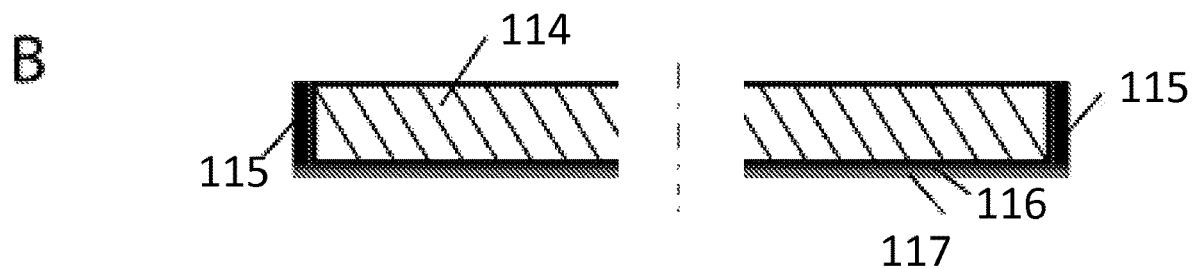

FIG. 11B shows the tool needed to place the membrane onto sample chamber. 114 is a solid piece of polycarbonate (a flat cylinder) fabricated by standard CNC milling process. 115 is another piece of solid polycarbonate, with the form of an annulus that can hold 114. There is a clearance of about 100 µm between 114 and 115 so that they can move relative to each other along their axis. A thin elastomeric membrane made of PDMS (116) was adhered to the surface of 114 and 115. PDMS naturally adheres weakly to plastic. A thin track-etched membrane with pore size about 20 microns (117) is adhered to the PDMS membrane 116.

Figure 11C:
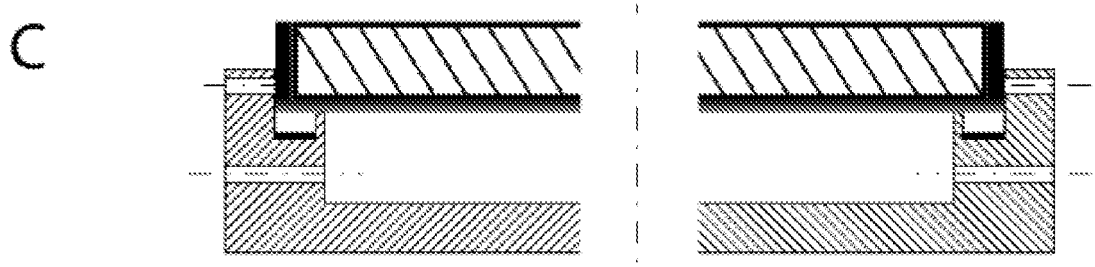

In FIG. 11C, the component depicted in FIG. 11B is placed on top of the component in FIG. 11A. The only contact at this point between the track-etched membrane 117 and the plastic component comprising the sample chamber in FIG. 11A is at the elevated ridge 113

Figure 11D:
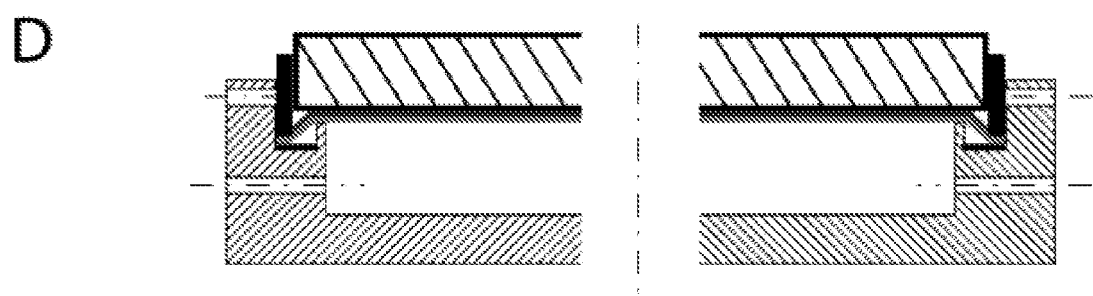

FIG. 11D depicts the step of assembly in which the polycarbonate perimeter 115 is pressed towards the sample chamber. Because 114 is holding the membranes against the ridge 113, only the ends of the membranes are pressed against the adhesive of 112.

Figure 11E:
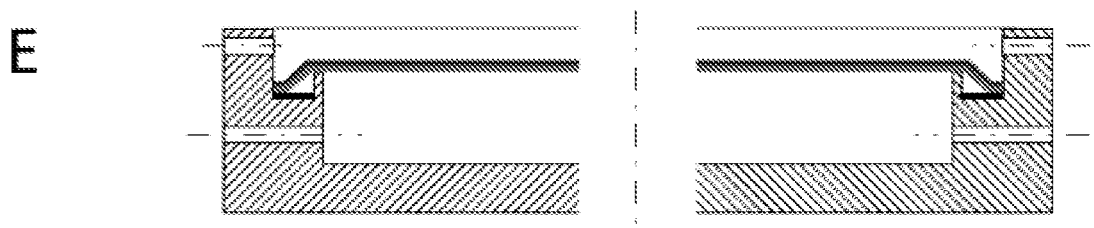

FIG. 11E depicts the removal of 114 and 115 from the device housing depicted in FIG. 11A. Only two membranes remain in place due to the adhesion of 117 to 113

Figure 11F:
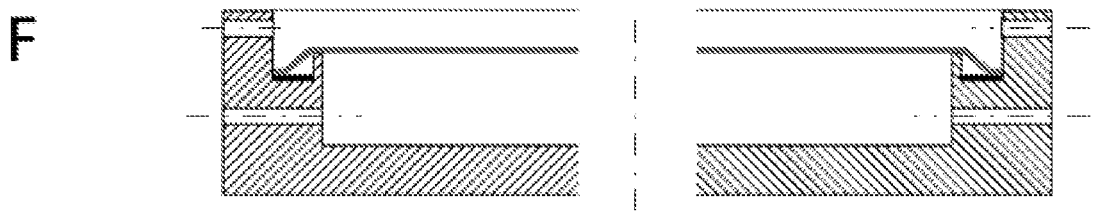

FIG. 11F depicts the fully attached PDMS membrane 118 is removed from track-etched membrane with tweezers.

Figure 11G:
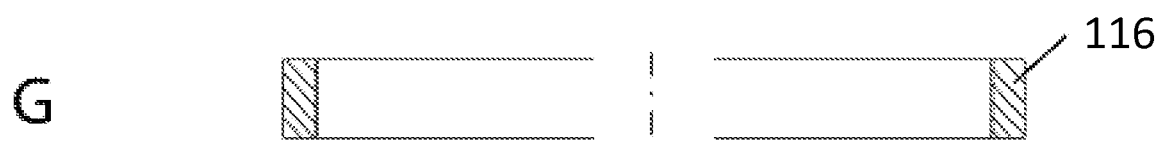

FIG. 11G depicts a plastic piece 116 with an annulus form similar to 114 but with different dimensions, so that it can be used to stretch the membrane.

Figure 11H:
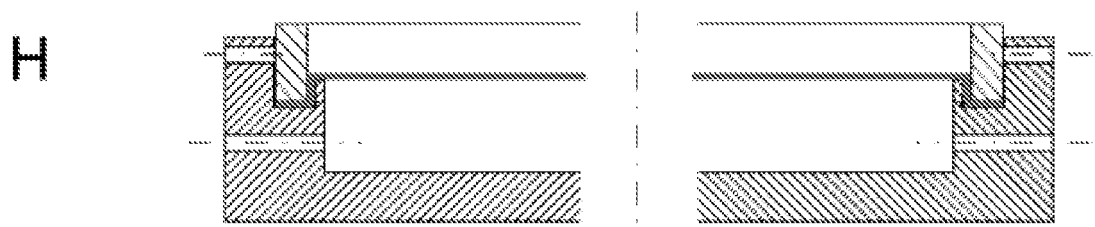

FIG. 11H depicts a step in which 116 is pressed against the membrane 117 and part 112. This action effectively stretches the membrane and adheres it at the same time to the device housing depicted in FIG. 11A.

Figure 11I:
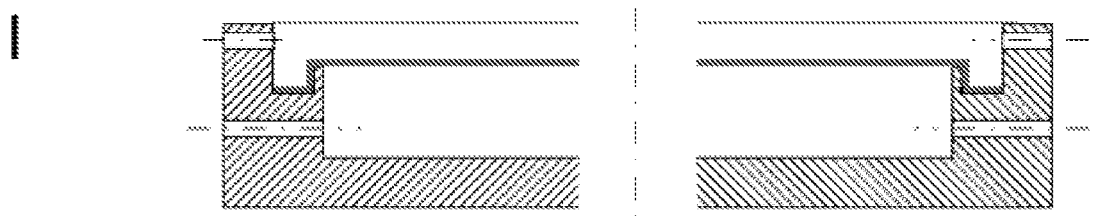

FIG. 11I depicts a final step in which 116 is removed from the device housing. The assembly comprising the device housing is depicted with a stretched membrane dividing a sample chamber on top of an isolation or collection chamber.

Example 8—Microliter-Scale Sample Chamber

Figure 12:
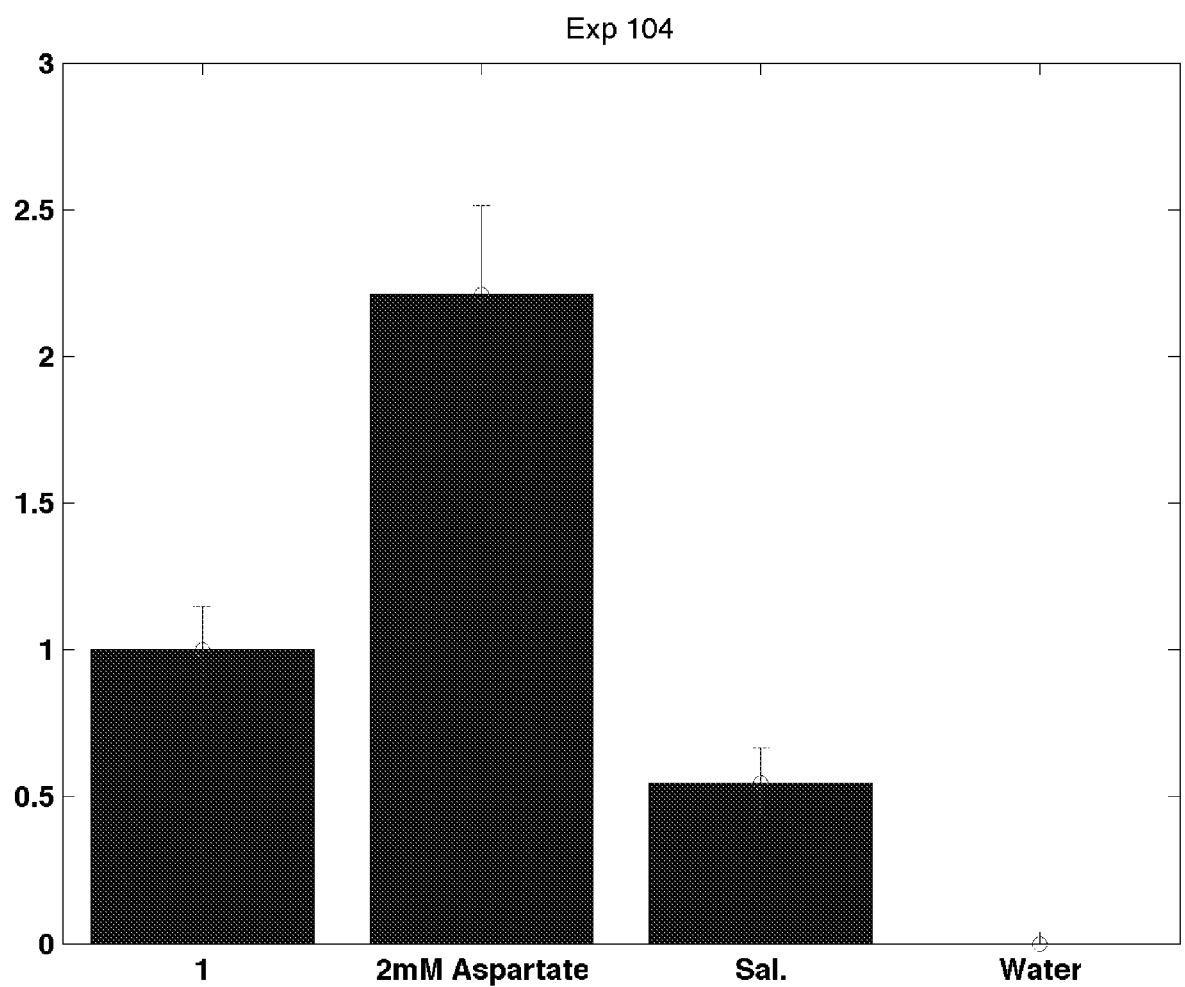
FIG. 12 depicts a graph of an experimental run of a separation method using a chemoattractant in an isolation chamber.

A device was constructed similar to the device shown in FIG. 9. Experimental and control separation runs were performed in the device and results recorded as disclosed below. FIG. 12 depicts an experimental run on the device in which 2 mM of alpha-methylaspartate (chemo-attractant) was diluted in chemotaxis buffer was introduced in the extraction chamber. *S. Typhimurium* in mid-exponential growth phase in cell media was introduced in the sample chamber with a volume of about 110 µL. Deionized water was introduced in the repellent chamber. After 30 minutes, the contents of each chamber was recovered and the amount of bacteria in each chamber counted. The graph shows the concentration of bacteria in each chamber normalized to the initial concentration introduced in the sample chamber. The results show that the concentration of bacteria in the extraction chamber was about 2 times higher than the initial concentration, and no bacteria were found in the repellent chamber.

Figure 13:
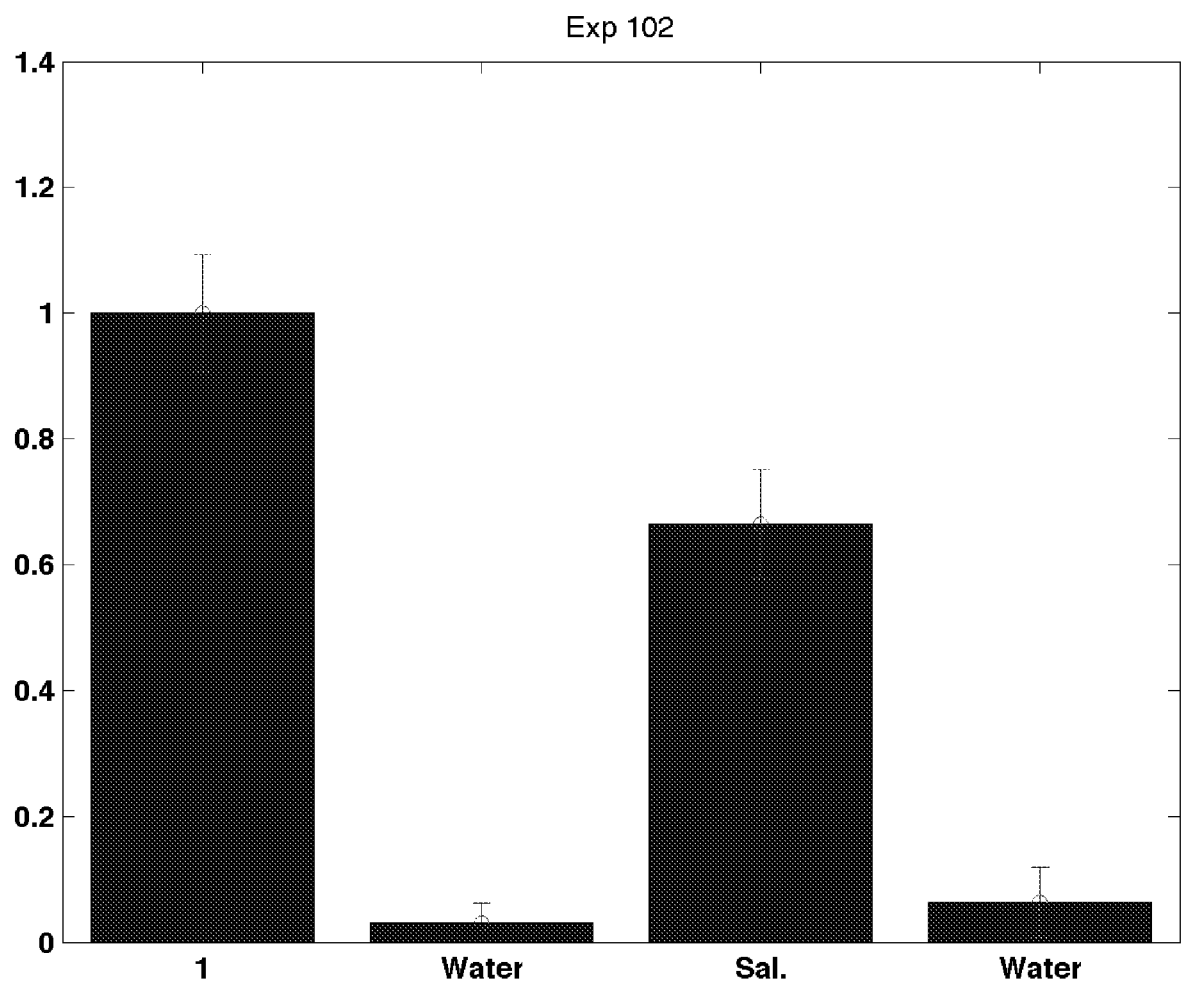
FIG. 13 depicts a graph of an control run of a separation method using the device utilized in FIG. 12 without using a chemoattractant in an isolation chamber.

FIG. 13 depicts a control experiment without chemoattractant, just *S. Typhimurium* in the sample chamber, and deionized water in the other two chambers.

Figure 14:
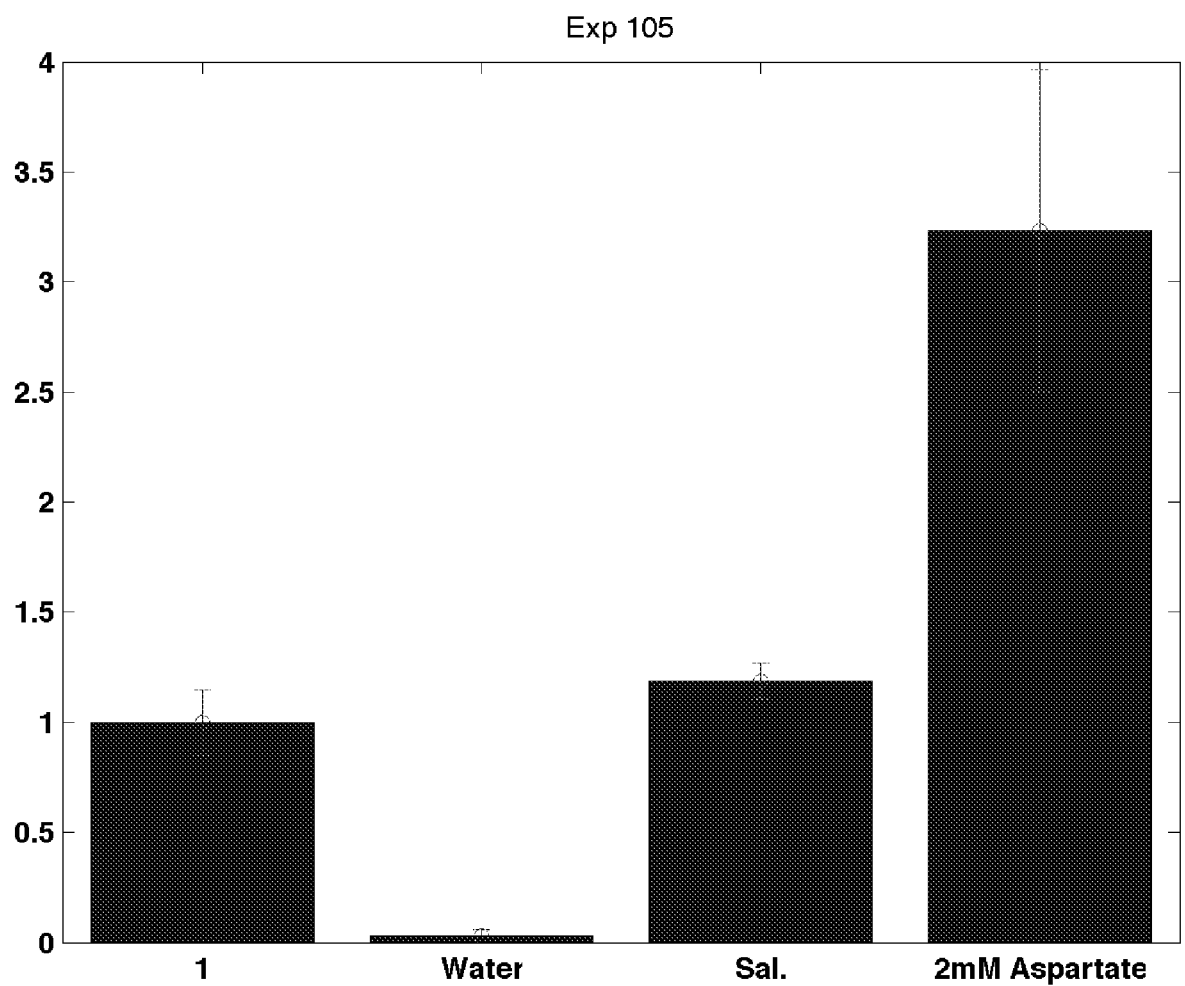
FIG. 14 depicts a graph of as second experimental run of a separation method using the device utilized in FIG. 12 with using a chemoattractant in an isolation chamber positioned on the opposite side of the device as compared to the position of the isolation chamber utilized in FIG. 12.

FIG. 14 depicts the result from a similar experiment as the experiment depicted in FIG. 12, except that the chemoattractant was filled in the opposite chamber. The result of FIG. 14 show the consistency of the bacterial cells to tend toward the chemoattractants from small volume sample chambers.

The invention claimed is:
1. A device comprising:
 (a) a first chamber;
 (b) a second chamber comprising a buffer solution and at least one chemoattractant;
 (c) a third chamber adjacent to and fluidically connected to the first chamber; and

(d) a membrane connecting the first and second chambers and defining an interface between the first and second chambers;

wherein the membrane comprises at least one of the following: (a) from about 3 µm to about 50 µm in thickness; (b) pore sizes from about 5 µm to about 100 µm wide; and (c) a pore density from about $4 \times 10^4$ pores/cm$^2$ to about $4 \times 10^5$ pores/cm$^2$;

wherein the first chamber, second chamber, and membrane are free of an electrode capable of creating an electric field within the first or second chamber; and the third chamber comprises one or a combination of chemorepellants chosen from:

acetate, aspartate, benzoate, ethanol, leucine, phenol, tryptophan, valine, H+, OH−, citrate, maltose, Co2+, and Ni$^2$.

2. The device of claim 1, wherein the device is free of a pressure source that increases pressure within the first chamber sufficient to transfer a volume from the first chamber to the second chamber; or free of any source of microfluidic flow within the first chamber.

3. The device of claim 1, wherein the first chamber has at least one fluid opening.

4. The device of claim 1, wherein the first chamber has a volume from about 25 mL, to about 100 mL.

5. The device of claim 1, wherein the second chamber comprises at least one chemorepellent.

6. The device of claim 1, wherein the first chamber, the second chamber, and the repellant layer are stacked in a vertical orientation such that the first chamber is positioned between the second chamber and the third chamber.

7. The device of claim 1, wherein at least one of the first chamber, the second chamber, and/or the repellant layer are from about 1 to about 10 millimeters in height.

8. The device of claim 1, wherein each of the first chamber, the second chamber, and the third chamber comprises an independently addressable fluid inlet for receiving fluid.

9. The device of claim 1, wherein fluid communication between the first chamber and the second chamber is only through the pores of the membrane.

10. A method of isolating a pathogen from a sample comprising: placing one or a plurality of samples into the first chamber of the device of claim 1; wherein the device comprise a chemoattractant or chemorepellent in the first chamber; and allowing a time period to elapse sufficient for a bacterial cell in the one or plurality of samples to move from the first chamber to the second chamber due to the a concentration gradient of the at least one chemoattractant or the chemorepellent present in the first chamber.

11. A method of detecting a bacterial cell in a sample comprising:

placing one or a plurality of samples into the first chamber of the device of claim 1; and allowing a time period to elapse sufficient for a bacterial cell in the one or plurality of samples to move from the first chamber into the second chamber due to a concentration gradient of the chemoattractant or the chemorepellent present in the first chamber, and detecting the presence or absence of the bacterial cell in the second chamber.

12. The method of claim 11, wherein the presence or absence of the bacterial cell in the second chamber is detected by extracting the buffer solution from the second chamber after allowing the time period to elapse and detecting the presence or absence of the bacterial cell in the buffer solution.

13. The method of claim 12, wherein the presence or absence of the bacterial cell in the buffer solution is detected by performing a polymerase chain reaction on the buffer solution.

14. The method of claim 11, wherein the method is performed in less than 14 hours.

15. The method of claim 11 further comprising a step of exposing the one or plurality of samples to a concentration gradient of the chemoattractant or the chemorepellent after placing the one or plurality of samples in the first chamber but before allowing the time period to elapse.

16. The method of claim 11, wherein the one or plurality of samples comprise at least one of: a solid or semi-solid matrix, liquid wash from crop material, or concentrated fluid.

* * * * *